US007216038B2

(12) United States Patent
Vitaliano et al.

(10) Patent No.: US 7,216,038 B2
(45) Date of Patent: *May 8, 2007

(54) QUANTUM INFORMATION PROCESSING ELEMENTS AND QUANTUM INFORMATION PROCESSING PLATFORMS USING SUCH ELEMENTS

(76) Inventors: Franco Vitaliano, 4 Longfellow Pl., #2105, Boston, MA (US) 02114;
Gordana Vitaliano, 4 Longfellow Pl., #2105, Boston, MA (US) 02114

(*) Notice: Subject to any disclaimer, the term of this patent is extended or adjusted under 35 U.S.C. 154(b) by 296 days.

This patent is subject to a terminal disclaimer.

(21) Appl. No.: 10/661,465

(22) Filed: Sep. 11, 2003

(65) Prior Publication Data

US 2005/0059167 A1  Mar. 17, 2005

(51) Int. Cl.
*G01N 33/48* (2006.01)
*G01N 31/00* (2006.01)
*C12Q 1/68* (2006.01)
*C07K 1/00* (2006.01)

(52) U.S. Cl. ............................ 702/19; 435/6; 702/22; 530/350

(58) Field of Classification Search ............... None
See application file for complete search history.

(56) References Cited

U.S. PATENT DOCUMENTS

| | | | |
|---|---|---|---|
| 4,367,066 A | 1/1983 | Zellweger | 434/433 |
| 4,999,842 A | 3/1991 | Huang et al. | 372/45 |
| 5,287,377 A | 2/1994 | Fukuzawa et al. | 372/45 |
| 5,613,140 A | 3/1997 | Taira | 395/800 |
| 5,671,437 A | 9/1997 | Taira | 395/800 |
| 5,838,436 A | 11/1998 | Hotaling et al. | 356/345 |
| 5,940,193 A | 8/1999 | Hotaling et al. | 359/11 |
| 6,437,413 B1 | 8/2002 | Yamaguchi et al. | 257/421 |
| 6,456,994 B1 | 9/2002 | Tucci | 706/52 |
| 6,459,097 B1 | 10/2002 | Zagoskin | 257/31 |
| 6,472,681 B1 | 10/2002 | Kane | 257/14 |
| 7,033,834 B2 | 4/2006 | Valerio et al. | |
| 7,037,520 B2 | 5/2006 | Smyth Templeton | |
| 7,048,949 B2 | 5/2006 | Sligar et al. | |
| 7,060,291 B1 | 6/2006 | Meers et al. | |
| 7,063,860 B2 | 6/2006 | Chancellor et al. | |
| RE39,229 E | 8/2006 | Choo et al. | |
| 7,094,409 B2 | 8/2006 | Bachmann et al. | |
| 7,101,532 B2 | 9/2006 | Aikawa et al. | |
| 7,101,570 B2 | 9/2006 | Hope et al. | |
| 7,105,303 B2 | 9/2006 | Ralston et al. | |
| 7,108,863 B2 | 9/2006 | Zalipsky et al. | |
| 7,108,915 B2 | 9/2006 | Adams et al. | |
| 7,112,330 B1 | 9/2006 | Buonamassa et al. | |
| 7,112,337 B2 | 9/2006 | Huang et al. | |

OTHER PUBLICATIONS

Gelderblom. Assembly and morphology of HIV: potential effect of structure on viral function. AIDS, 1991, vol. 5, pp. 617-637.*
Stewart et al. Adenovirus structure by X-ray Crystallography and Electron Microscopy. Current Topics in Microbiology and Immunology, vol. 199, 1995, pp. 25-38.*

(Continued)

*Primary Examiner*—John S. Brusca
*Assistant Examiner*—Russell S. Negin

(57) ABSTRACT

The invention in various embodiments is directed to quantum information processing elements and quantum information processing platforms employing such elements. In one aspect, the quantum information processing elements are formed with self-assembling protein molecules.

56 Claims, 16 Drawing Sheets

OTHER PUBLICATIONS

Lee et al. Ordering of Quantum Dots using genetically engineered viruses. Science. May 3, 2002, vol. 296, pp. 892-895.*

Overman et al., "Raman Spectroscopy of filamentous bacteriphage Ff (fd, f1, M13): Assignment and structural interpretation of coat protein aromatics." Biophysical Journal, vol. 66, p. A 394, 1994, abstract.*

Zampighi et al. Polyhedral protein cages encase synaptic vesicles and particpate in ther attachment to the active zone. Journal of Structural Biology. vol. 119, pp. 347-359, 1997.*

Abe, E. (2001) "ESR on Shallow Donors in Ge," (PowerPoint Presentation).

Barenco et al. (1996) "A short introduction to quantum computation," www.qubit.org / library / intros / comp / comp.html.

Bayer, M. (Aug. 8, 2002) "One at a time, please," Nature 418:597-598.

Benjamin et al. (date unknown) "Towards Quantum Information Technology," www.qubit.org / library / intros / nano / nano.html.

Blatt, R. (2001) "Delicate information," Nature 412:773.

Borbat et al. (Apr. 19, 2002) "Protein Structure Determination Using Long-Distance Constraints from Double-Quantum Coherence ESR: Study of T4 Lysozyme," *J. Am. Chem. Soc.* 124: 5304-5314.

Brown J. (2000) "Minds, Machines and Multiverse (The Quest for the Quantum Computer)," Chapter 1, Simon & Schuster 2000.

Cheetham et al. (1996) "Inhibition of hsc70-catalysed clathrin uncoating by HSJ1 proteins," *Biochem J.* 319: 103-108.

Claeysen et al. (Nov. 18, 2002) "A Single Mutation in the 5-HT$_4$ Receptor (5-HT$_4$-R D100(3.32)A) Generates a G$_S$-coupled Receptor Activated Exclusively by Synthetic Ligands (RASSL)," *Journal of Biological Chemistry* 278: 699-702.

Claing et al. (2001) β-Arrestin-mediated ADP-ribosylation Factor 6 Activation and β$_2$-Adrenergic Receptor Endocytosis, *Journal of Biological Chemistry* 276: 42509-42513.

Coward et al. (1998) "Controlling signaling with a specifically designed G$_i$-coupled receptor," *Proc. Natl. Acad. Sci. USA* 95: 352-357.

Crotzer, V. L. et al. (2001) "The Role and Regulation of Clathrin in T cell Receptor Internalization," (Abstract) www.midwconfimmunol.org / Midwinter01 / posters / crotzer.html.

Deutsch et al. (1998) "Quantum Computation," www.qubit.org / library / intros / PhysicsWorld / PhysicsWorld.html, p. 1 only.

De Martini et al. (Oct. 24, 2002) "Experimental realization of the quantum universal NOT gate," Nature 419: 815-818.

DiVincenzo, D. (1996) "Gates and Circuits: Sleator-Weinfurter construction: V$^2$=U," *Phil Trans. R. Soc. Lond. A*: 9-18.

DiVincenzo, D. (1997) "Quantum Gates and Circuits," *Phil Trans. R. Soc. Land. A.*, Submitted.

DiVincenzo, D. (1998) Real and realistic quantum computers, *Nature* 393: 113-114.

Follstaedt et al. (2000) "Protein Adhesion on SAM Coated Semiconductor Wafers: Hydrophobic Versus Hydrophilic Surfaces," Sandia Report SAND_2000-3016.

Gad, H. et al. (2000) "Fission and uncoating of synaptic clathrin-coated vesicles are per turbed by disruption of interactions with the SH3 domain of endophilin," Neuron 27:301-312 (Abstract only).

Gad, H. (2000) "Synaptic vesicle endocytosis studied in a living synapse," (Ph.D. Thesis) Karolinska Institute. (conclusions drawn from Ph.D. thesis).

Gershenfeld et al. (1998) "Quantum Computing with Molecules," *Scientific American*. Jun. 1998 (www.media.mit.edu/physics/publications/papers/98.06.sciam/0698gershenfeld.html).

Gisin, N. (Oct. 24, 2002) "NOT logic," Nature 419: 797-798.

Greene et al. (2000) "Complete Reconstitution of Clathrin Basket Formation with Recombinant Protein Fragments: Adaptor Control of Clathrin Self-Assembly," *Traffic* 1: 69-75.

Hameroff et al (1998) "Quantum Theory and Human Consciousness," 47-62.

Hardy et al. (2000) "Universal Manipulation of a Single Qubit," Centre for Quantum Computation, Clarendon Laboratory, Department of Physics, University of Oxford.

Harneit et al. (Jul. 20, 2002) "Architectures for a Spin Quantum Computer Based on Endohedral Fullerenes," *Phys. Stat. Sol.* 233: 453-461.

Haucke V., "Molecular Mechanisms of Endocytosis," INABIS'98.

Hubbell et al. (1998) "Recent advances in site-directed spin labeling of proteins," *Current Opinion in Structural Biology* 8: 649-656.

Kanaseki et al. (1969) "The Vesicle in a Basket: A Morphological Study of the Coated Vesicle Isolated from the Nerve Endings of the Guinea Pig Brain, with Special Reference to the Mechanism of Membrane Movements," *Journal of Cell Biology* 42: 202-220.

Kirchhausen, T. et al. (1997) "Linking cargo to vesicle formation: receptor tail interactions with coat proteins," *Current Opinion in Cell Biology* 9: 488-495.

Laflamme et al. (Aug. 22, 2002) "NMR GHZ" (www.arxiv.org).

Leuenberger et al. (2001) "Quantum computing in molecular magnets," Department of Physics and Astronomy, University of Basel, Switzerland.

Liu et al. (1995) "Regulation of Clathrin Assembly and Trimerization Defined Using Recombinant Triskelion Hubs," *Cell* 83: 257-267.

Liu et al. (2001) "Observation of coherent optical information storage in an atomic medium using halted light pulses," *Nature* 409: 490-493.

Mekis, A. et al. (1995) "Ray chaos and Q-spoiling in Lasing Droplets," *Phys. Rev. Lett.* 75:2682-2686.

Mullins, J. (2001) "The Topsy Turvey World of Quantum Computing," *IEEE Spectrum*: 42-49.

Nöckel, J. U. et al. (1996) "Chaotic Light: A Theory of Asymmetric Resonant Cavities," Optical Processes in Microactivities, World Scientific Publishers, 1996.

Nöckel, J. U. et al. (1994) "Q-spoiling and Directionality in Deformed Ring Cavities," *Optics Letters* 19: 1693-1695.

Oskin et al. (Jan. 2002) "A Practical Architecture for Reliable Quantum Computers," *Computer*: 79-87.

Owen, D.J. (2000) "The structure and function of the β2-adaptin appendage domain," EMBO Journal 19: 4216-4227.

Preskill, J. (1997) "Reliable Quantum Computers," (manuscript) California Institute of Technology. (www.arxiv.org).

Redfern, C. (1999) "Conditional expression and signaling of a specifically designed G$_i$-coupled receptor in transgenic mice," *Nature Biotechnology* 17: 165-169.

Recher et al. (2000) "Quantum Dot as Spin Filter and Spin Memory," *Physical Review Letters*: 85 1962-1965.

Rieffel et al. (2000) "An Introduction to Quantum Computing for Non-Physicists," *ACM Computing Surveys* 32: 300-335.

Scearce-Levie et al. (2001) "Engineering receptors activated solely by synthetic ligands (RASSLs)," *Trends in Pharmacological Sciences* 22: 414-420.

Shih, W. et al. (1995) A Clathrin-binding Site in the Hinge of the β2 Chain of Mammalian AP-2 Complexes, *The Journal of Biological Chemistry* 270: 31083-31090.

Steane, A. (1996) "Quantum Error Correction," www.qubit.org / library / intros/QEC.html.

Steane, A. (1997) "Quantum Computing," Department of Atomic and Laser Physics, University of Oxford, Clarendon Laboratory: 1-65.

Steane, A. (1998) "Quantum Computing," *Reports on Progress in Physics* 61: 117-173.

Steane et al. (2000) "Physicists Triumph at Guess My Number," *Physics Today*, 35-39.

Takei et al. (1998) "Generation of Coated Intermediates of Clathrin-Mediated Endocytosis on Protein-Free Liposomes," Cell 94: 131-141.

Twamley, J. (Oct. 30, 2002) "Quantum cellular automata quantum computing with endohedral fullerenes," (manuscript) (www.arvix.org).

Vitaliano, F. (2001) "The Next Big Thing That Will Change Absolutely Everything," www.vxm.com/Speed.quantum.html.

Vitaliano, F. (Jun. 18, 2002) "VXMaia: A New Quantum Computing System," (PowerPoint Presentation).

Vitaliano, F. (Oct. 23, 2002) "VXMaia: A New Quantum Computing System for Biotech," (PowerPoint Presentation).

Vitaliano, F. (Feb. 2003) "VXMaia: A New Quantum Computing Platform" (PowerPoint Presentation).

Vitaliano, F. (Sep. 2003) "EXQOR: A New NBIC Platform" (PowerPoint Presentation).

Vitaliano, F. (Feb. 2004) "ExQor: A New NBIC Platform".

Vitaliano et al. (Jan. 29, 2004) "Clathrin and Endocytosis" (PowerPoint Presentation).

Volovich I.V. (1999) "Atomic Quantum Computer," (manuscript) (www.arxiv.org).

Vrijen et al. (1999) "Electron Spin Resonance Transistors for Quantum Computing in Silicon-Germanium Hetero-structures," (manuscript) (ww.orxiv.org).

Ybe et al. (1998) "Clathrin self-assembly is regulated by three light-chain residues controlling the formation of critical salt bridges," *The EMBO Journal* 17: 1297-1303.

Ybe et al. (1999) "Clathrin Structure Reveals a Motifs for Self Assembly," www.als.lbl.gov / als / science/sci_archive / clathrin.html.

Ybe et al. (2000) "Molecular Structures of Proteins Involved in Vesicle Fusion," *Traffic* 1: 474-479.

"Electron Spin Resonance (ESR)," (2000) Physics 77, Experiment 6.

"pET-15b Vector," (1998), Novagen Catalog.

"pET-23a-d(+) Vectors," (1998), Novagen Catalog.

* cited by examiner

QUANTUM INFORMATION PROCESSING ELEMENTS AND QUANTUM INFORMATION PROCESSING PLATFORMS USING SUCH ELEMENTS

FIELD OF THE INVENTION

The invention relates generally to the field of quantum computers, and more specifically, in one embodiment, to quantum information processing (QIP) elements formed from self-assembling protein molecules. In another embodiment, the invention relates to a quantum information processing platform, such as a quantum computer platform, biomedical platform, telecommunication platform and the like, using such elements.

BACKGROUND OF THE INVENTION

Classical computers operate using classical physics principles and include transistors, semiconductors, and integrated circuit technology. In order to achieve greater speed and capability, classical computers increasingly use smaller and smaller wires and logic gates on the order of microns wide. As classical computer chips reach the nanometer scale and logic gates consist of a few atoms, classical limits are approached, and quantum mechanical principles and phenomena begin to dominate. This physical limit presents a barrier to the speed with which computations may be carried out by a classical computer.

Quantum computing utilizes the principles of quantum physics, rather than classical physics, to store and manipulate data, and operates on two principles having no corollary in classical physics: superposition and entanglement. Just as a binary digit, or "bit," is the basic unit of information in a classical computer, a quantum bit, or "qubit," is the basic unit of information in a quantum computer. A qubit generally is a system that has two degenerate quantum states. Unlike a classical bit, which exists in one of two states (0 or 1), the qubit can exist in a superposition of both of its degenerate states. As a result, a quantum computer comprised of N qubits can undertake $2^N$ computations in a single step. Thus, as more qubits are added to a quantum computer, the computing power increases exponentially.

The superposition or "coherence" state of a qubit is difficult to maintain because interactions with the surrounding environment cause the qubit to rapidly decay into a classical or "decoherent" state, which destroys the qubit's ability to perform computations. Therefore, a primary obstacle to building a viable quantum computer is maintaining the qubit in its coherent state long enough to do useful work.

Entanglement refers to pairs of particles that have interacted at some point in the past. Entangled particles that are spatially isolated remain related. More particularly, the state of both particles of an entangled pair is always simultaneously determined. For example, measurement of a first particle of an entangled pair collapses the first particle's wave function into a single observable quantity and simultaneously determines the observable state of the second particle of the entangled pair. Pauli's exclusion principle prevents both particles of the entangled pair from occupying the same state. Thus, if one particle of the pair is determined to have a logic 1 state, the other must have a logic 0 state.

Several quantum information processing (QIP) systems for use in quantum computers are known. Each of these systems, however, has distinct disadvantages. One system uses well-established nuclear magnetic resonance (NMR) techniques to store and read information from the degenerate nuclear spin states of molecules in solution. Such a system has been used to complete basic mathematical functions, such as factoring the number 15. However, a NMR-based quantum computer requires a large number of molecules in solution to complete even relatively simple functions, and the system suffers from an attenuated signal-to-noise ratio as the number of molecules increases. Thus, the complexity of calculations that a NMR-based quantum computer is capable of carrying out may be limited.

Another QIP system uses a $C_{60}$ Fullerene molecule in which an atom or molecule having an unpaired electron is encased, creating an endohedral Fullerene, and encodes data in the spin states of the unpaired electrons using electron spin resonance (ESR) techniques. However, charge transfer from the enclosed atom or molecule to the Fullerene cage often rapidly occurs, which leads to quantum decoherence and loss of the information encoded in the unpaired electron. Charge transfer to the Fullerene cage also limits the make up of atoms and molecules that may be enclosed. In addition, the relatively small size of the Fullerene cavity limits the types of atoms and molecules that may be enclosed. Furthermore, inserting an atom or molecule inside the cavity of a Fullerene molecule is difficult, and the success rate for the uptake of these cargo elements is poor. These factors, coupled with the high cost of the materials needed to fabricate doped Fullerene molecules, limit the potential size and computing power of a Fullerene-based quantum computer.

An alternative QIP system utilizes an electromagnetic ion trap to store and manipulate ions. Information is encoded by manipulating the electronic state of the trapped ion's valence electrons. However, ion trap systems must operate at extremely low temperatures to maintain quantum coherence long enough to be useful, thus requiring an elaborate cooling system.

Other QIP systems make use of "quantum dots" which include small amounts of a semiconducting material enclosed within another semiconducting material. Information is encoded in the quantum dot by manipulating the energy state of particles within the enclosed semiconducting material. Existing QIP systems involve embedding several quantum dots in a solid-state microdisk. However, the excess microdisk material that surrounds the quantum dot contributes to contaminating background radiation and shortened coherence times, which degrades the performance of the system and limits the scale of a quantum dot-based quantum computer.

Semiconductor-based QIP systems typically involve a "top down" assembly approach, and employ some form of lithography and replication. Top down approaches can be time consuming, expensive and wasteful of materials.

Thus, there exists a need for an improved QIP element that avoids the shortcomings of conventional designs.

SUMMARY OF THE INVENTION

The invention, in one aspect, remedies the deficiencies of the prior art by providing a nanoscale quantum information processing (QIP) element, which may be employed in a scalable quantum information processing platform. A platform according to the invention may be used for example in quantum computing, quantum networks, and quantum cryptography.

In one embodiment, the QIP element is formed from one or more cargo elements contained within a self-assembling protein cage. In some configurations, cargo elements include one or more qubits. In other embodiments, the cargo elements are exclusively non-qubit cargo elements. One advantage of the invention is that it inhibits charge transfer between the cage and its enclosed qubits. An advantage of inhibiting charge transfer is that it reduces limitations on the make up of enclosed cargo elements. According to one feature, the QIP element is formed using a "bottom-up" fabrication approach. According to such an approach, various self-assembling and self-directed approaches are employed. Using such an approach, the QIP platform can be formed from the ground up, one element at a time, for highly specific nano-scale tasks. Another advantage of the "bottom-up" fabrication approach is that it reduces the amount of superfluous material that surrounds each qubit within the cavity, reducing the qubit's exposure to contaminant background radiation and thereby improving the functional effectiveness of a qubit. A further advantage of the bottom-up self-assembly of the QIP element is that it enables the ordered placement of qubits with minimal inter-qubit spacings, thus avoiding a significant drawback to the use of endohedral Fullerenes and also other prior art QIP approaches, such as precise ion implantation through masks, and manipulation of single atoms on the surface of silicon.

A further advantage of the invention is that it provides a structure that maintains quantum coherent states long enough to do useful work. In addition, the invention can maintain quantum coherent states at room temperature, which eliminates the need for elaborate cooling mechanisms. In one embodiment, the cavity defined by the cage is larger than those described in the art, so the invention can incorporate a larger variety and number of cargo elements. According to another feature, the proteins that form the cage can be bio-engineered using commercially-available biotechnology tools to contain different cargo elements, which makes the invention more versatile and cost-effective than the existing art. Unlike existing systems where the cargo elements must be inserted into an existing structure, the invention, in one embodiment, provides individual protein molecules that self-assemble around the cargo elements to form the cage, which makes the addition of cargo elements easier.

In general, in one aspect, the invention features a QIP element that includes a cage defining a cavity in which one or more cargo elements are located. The cage is formed from a plurality of self-assembling protein molecules. In a further embodiment, at least one of the cargo elements is or includes a qubit that is programmable into a plurality of logical states.

In various embodiments of the invention, the cage is substantially larger than one nanometer in diameter, including sizes that can exceed about 50 or even about 100 nanometers in diameter. According to one embodiment, the self-assembling cage is a functional substitute for $C_{60}$, $C_{80}$, and other types of Fullerene cages, including endohedral Fullerenes. Furthermore, Fullerenes may be carried as ordered cargo within the self-assembling protein cage.

The relatively large size of the cage, as compared to the existing art, allows for a wider variety of possible cargo elements, which enables the invention to store and read information using a variety of techniques known in the art, including, but not limited to, electron spin resonance (ESR), nuclear magnetic resonance (NMR), quantum and photonic dots, efficient linear-optical quantum computing, and electromagnetically induced transparency techniques.

Preferably, the cage has an icosahedral geometry. In some embodiments the cage is symmetric with respect to a plane. In one embodiment, ordered qubits are linearly positioned at vertices along a single plane using circulant ordering. In one particular embodiment, the self-assembling protein molecules that make up the cage are clathrin molecules, which may be biologically engineered.

According to one embodiment, a qubit cargo element contains an unpaired electron, and the plurality of logical states into which the qubit can be programmed is defined, for example, by the spin polarization of the unpaired electron, or by the valence state of the unpaired electron. One example of this embodiment is a molecule containing a free radical, such as nitroxide. In an alternative embodiment, the plurality of logical states into which the qubit can be programmed are defined by the nuclear spin polarization of particular atoms within the qubit. In another alternative embodiment, the qubit is photon-based, and the plurality of logical states into which the qubit can be programmed is defined by the polarization of the photons emitted by the qubit.

According to one application, the qubit can be programmed into one of a plurality of logical states by one or more pulses of electromagnetic energy. The frequency of the electromagnetic energy may be, for example, in the radio frequency region, the UHF region, or the microwave region.

In some configurations, the cage contains a single cargo element, while in other configurations it contains multiple cargo elements. In some cases, each of the cargo elements is or includes a qubit that is programmable into a plurality of logical states. Alternatively, some of the cargo elements are or include non-qubit elements.

According to one feature, the cargo elements may include one or more therapeutic or diagnostic agents. Such agents may be, for example, nano-structured and/or may include chemical, biological and/or metallic materials. The agents may be or include organic or inorganic materials or a combination thereof.

According to another feature, one or more cargo elements may be or include nanoscale diagnostic devices, biosensors, and/or prostheses, in any qubit/non-qubit combination. Some or all of the qubit and non-qubit cargo elements may operate under the control and influence of other QIP elements, and altogether may comprise a scalable quantum information processing platform for QIP-based biomedicine.

According to one illustrative configuration, one or more non-qubit cargo elements that interfere with qubit programmability and/or induce quantum decoherence if carried in the same protein cage as a qubit cargo element is instead carried in a separate QIP element protein cage that exclusively carries non-qubit cargo elements, thereby inhibiting disruptive cargo interference with QIP operations. Such non-qubit-only cages may be functionally or physically linked with other QIP element cages carrying programmable qubit cargo elements.

In another aspect, the protein cage features no elements at all. According to one embodiment, empty self-assembling cages include highly ordered scaffolding and a charge transfer limiting substrate material for self-assembling multilayer, multi-QIP element systems. In another embodiment, empty cages also may facilitate the self-aligning of cargo carrying QIP elements with respect to one another.

As a general aspect, a QIP element and its qubit and non-qubit cargo elements may take any suitable form, and multiple QIP element embodiments may be further combined in any suitable manner to create multifunction, scalable quantum information processing platforms.

The QIP element, in one configuration, includes receptor molecules for capturing and ordering the placement of the cargo elements inside the cage.

The QIP element also includes adapter molecules disposed between the receptor molecules and the cage to couple the receptor molecules to the cage inside the cavity.

In another QIP element configuration, molecular or chemical bonding is used to attach directly cargo elements to the cage in an ordered arrangement. In other QIP element configurations, a short molecular tether is used to attach cargo elements to the cage in an ordered arrangement. In other QIP element configurations, receptors, molecular tethers, and direct bonding are used in combination to attach and orderly position cargo elements within the cage.

In some configurations, the QIP element includes a vesicle located within the cage, with one or more cargo elements located within the vesicle. In such a configuration, receptor molecules extend through the vesicle to capture and order one or more cargo elements within the vesicle. According to one embodiment, the vesicle is protein-based. According to a feature of this embodiment, the protein-based vesicle inhibits charge transfer between the vesicle and its enclosed cargo elements.

In another configuration, cargo elements within a vesicle may not be attached to receptors, and the cargo may be free floating within the cavity of a non-permeable vesicle, for example, in an encapsulated fluid or gas. In other configurations, both the self-assembling cage and vesicle may be devoid of cargo. According to one feature, the cage, cargo elements within the cage, and/or a vesicle within the cage including its cargo elements, respond to certain external and/or internal stimuli, which can be, for example, mechanical, chemical, biological, photonic, sonic, thermal, or electrical in nature. An example of such a stimulus response is deformation of the geometry of a cargo element within a cage, deformation of a vesicle within a cage, and/or deformation of the cage itself.

In general, in another aspect, the invention features a scalable QIP platform that includes one or more embodiments of the QIP elements described above. Preferably, the scalable QIP platform also includes an encoder for programming the qubits of at least a subset of the quantum processing elements, and a decoder for reading information from the qubits of at least a subset of the quantum processing elements.

In general, in another embodiment, a QIP element and a QIP platform may be physically and/or functionally cooperative with other suitable types or forms of materials, substances, components, devices, or systems, in vitro and/or in vivo.

In general, in a further aspect, the invention is directed to a method of forming a QIP element, including the steps of forming in vitro from self-assembling protein molecules, such as clathrin molecules, a cage defining a cavity, and locating one or more cargo elements within the cavity. In one embodiment, the method includes locating at least one qubit, programmable into a plurality of logical states, within the cavity.

In general, in another aspect, the invention is directed to a method of forming a scalable quantum information processing platform, including the steps of providing one or more embodiments of the QIP elements described above, programming the qubits included in one or more QIP elements using an encoder, and reading information from the QIP elements using a decoder.

BRIEF DESCRIPTION OF THE DRAWINGS

The foregoing and other aspects of the invention may be more fully understood from the following description, when read together with the accompanying drawings in which like reference numbers indicate like parts.

DESCRIPTION OF THE ILLUSTRATIVE EMBODIMENTS

Figure 1:
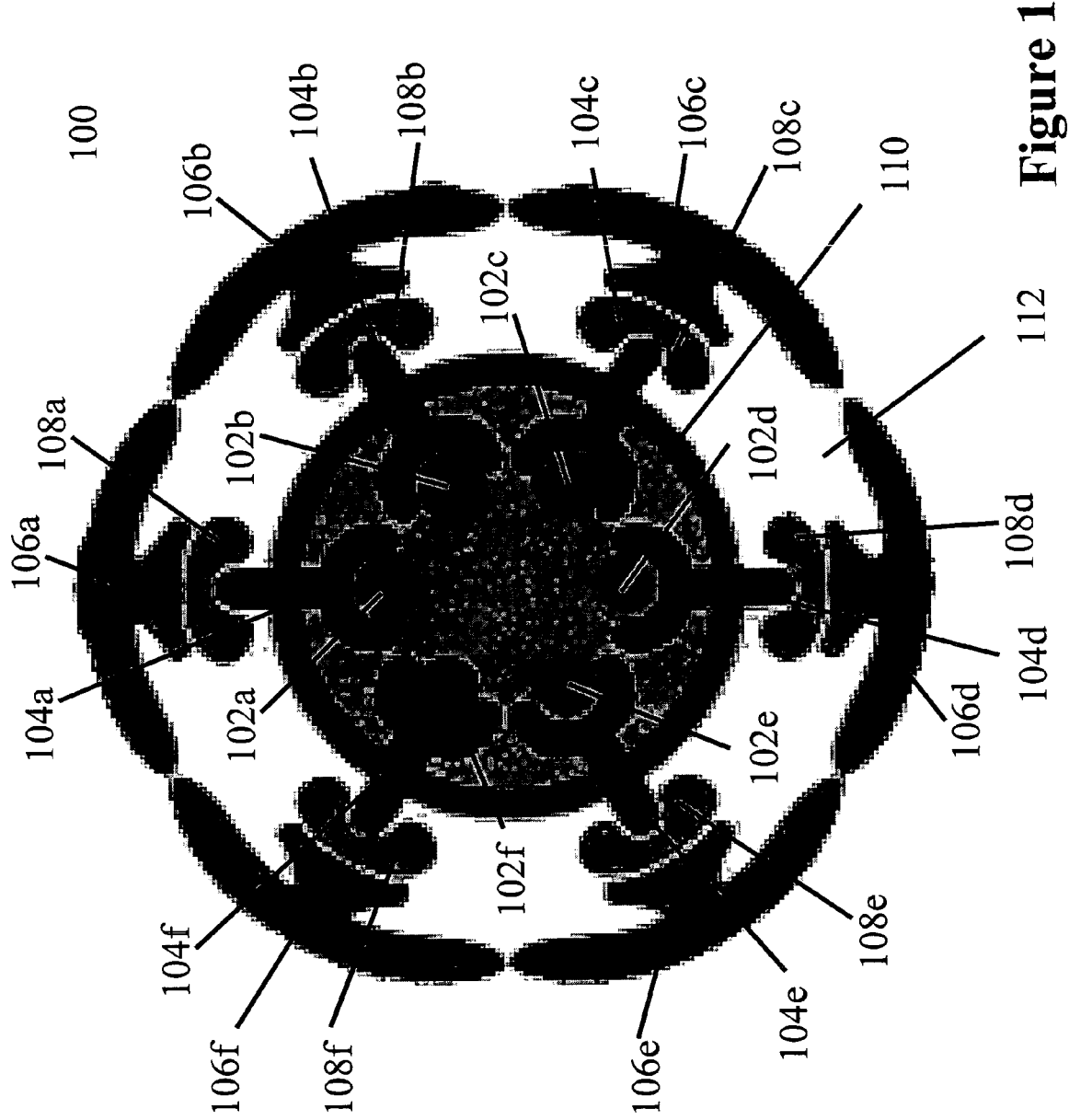
FIG. 1 is a conceptual cross-sectional view of a quantum information processing (QIP) element according to an illustrative embodiment of the invention.

FIG. 1 is a conceptual cross-sectional view of a quantum information processing (QIP) element 100, according to an illustrative embodiment of the invention. The QIP element 100 includes one or more cargo elements 102a–102f, a plurality of receptor molecules 104a–104f, a plurality of protein molecules 106a–106f formed into a cage 106, and a plurality of adapter molecules 108a–108f. The protein molecules 106a–106f self-assemble in vitro to form the cage 106 that defines a cavity 112.

As shown, the receptor molecules 104a–104f each bond with a respective cargo element 102a–102f, and the adapter molecules 108a–108f bond the receptor molecules 104a–104f to the protein molecules 106a–106f, respectively.

The bonding may be either covalent or non-covalent—the latter type including ionic interactions, hydrophobic interactions, or hydrogen bonds—depending on the application, system design, receptor design, cargo type and/or the interaction/application environment. Some G protein-coupled receptors (GPCRs) use covalent bonds, which are individually strong (e.g., it takes energy to break the covalent bond). In some instances, the clathrin molecule attaches covalently to the solution termini of alkanethiol SAMs via covalent bonding. In other illustrative embodiments, electrostatic (ionic) bonding may be employed.

Most GPCRs do not form covalent bonds with their ligand when bound in the receptor. Noncovalent interactions are individually weak but collectively strong, such as with a substantial number of noncovalent interactions working together to hold a structure together, or a surface topography that enables substantial areas of two interacting surfaces to approach each other closely. Ligands generally bind to receptors via ionic, hydrophobic hydrogen and van Der Waal bonds.

Cage 106 can be naturally occurring or biologically engineered and/or can use synthetic proteins in whole or in part. Also, the receptor molecules 104a–104f can be naturally occurring or biologically engineered and/or can use synthetic proteins in whole or in part to recognize specific cargo elements 102a–102f. Likewise, the adapter molecules 108a–108f can be naturally occurring or biologically engineered and/or can use synthetic proteins in whole or in part to recognize and couple to particular receptor molecules 104a–104f.

Optionally, the protein cage 106 forms to enclose (e.g., to "coat") a vesicle 110 within the cavity 112. ARF-GTP, appropriate lipids, and cytosolic factor(s) are used for AP-1 clathrin coated vesicle assembly. Recruitment of AP-1 (Assembly Polypeptides) onto liposomes is ARF-dependent and facilitated by cytosolic ARF Guanine Nucleotide-Exchange Factor (GEF). Lipid composition is important and modulates ARF and AP-1 binding. The vesicle 110 can be formed, for example from naturally occurring membrane material, such as L-a-Phosphatidylinositol-4,5-bisphosphate or from synthetic membrane materials, such as a fully synthetic liposome like one containing DOPC DOPE cholesterol or from a mixture of both, for example, from synthetic lipids such as L-a-Phosphatidylcholine (PC) from soybeans containing 20% PC (Sigma P5638).

The adapter molecules tether the vesicle 110 to the cage 106. The adapter molecules 108a–108f, in turn, bond to receptor molecules 104a–104f disposed around the periphery of the vesicle 110. According to the illustrative embodiment, the receptor molecules 104a–104f extend through the vesicle 110 to capture the cargo elements 102a–102f.

In one illustrative embodiment, the self-assembling protein molecules 106a–106f are clathrin molecules, and the clathrin cage 106 can be of any suitable size. According to the illustrative embodiment, the clathrin cage 106 has a diameter greater than about one nanometer. In various other illustrative embodiments, the clathrin cage 106 can have a diameter between about one nanometer and about fifty nanometers, a diameter between about fifty nanometers and about one hundred nanometers, or a diameter greater than about one hundred nanometers. The vesicle 110 may have any suitable size, such that its diameter is less than that of the clathrin cage 106.

In another illustrative embodiment, the cargo elements 102a–102f or the vesicle 110 include an asymmetric resonant cavity (ARC) high-Q ("whispering gallery mode") nanolaser.

The highest Q optical resonators are dielectric microspheres or nanospheres in which the high Q modes are created by a total internal reflection of light circulating just inside the sphere. These high Q modes are known as whispering gallery modes or alternatively as morphology-dependent resonances. If the dielectric is a liquid droplet containing an appropriate dye then the droplet acts as a high Q micro- or nano-resonator to support lasing action when optically pumped.

The Q factor within the microsphere or nanosphere remains high up to a critical deformation and then decreases rapidly. Beyond this critical deformation, the laser light emission from the deformable microcavity or nanocavity becomes highly directional and controllable. This ray optics model for deformable droplets has evolved to generally describe the spoiling of the high-Q (whispering gallery) modes of deformable ring-shaped cavities as they are deformed from perfect circularity. A sharp threshold has been found for the onset of Q-spoiling as predicted by the KAM theorem of non-linear dynamics. Beyond a critical deformation the escaping light emerges in certain specific directions that may be predicted. The deformations considered can be quite large, ranging from 1–50% of the undeformed radius, assuming that they maintain the convexity of the cavities. Such "asymmetric resonant cavities" (ARC) possess unique advantages, such as:

1. The ability to tune the Q-value and resonant frequency of the ARC by appropriate deformations.
 2. When deformed in situ, designing a Q-switched ARC laser.
 3. The ability to couple a high-Q/WG mode out of the ARC with strong directionality.

In one illustrative ARC nanolaser embodiment, a dyed droplet with or without additive scattering particles is carried within cargo elements 102a–102f that are designed to be cavity forming and non-permeable, and/or the droplet is carried within a cavity forming, non-permeable vesicle 110 within cage 106. Forces, for example, photonic, mechanical, fluidic, thermal, sonic, or electromagnetic, but not limited to such, deform the cavity forming cargo elements 102a–102f and/or deform the cavity forming vesicle 110 within the cage 106. Accordingly, the dyed droplet carried within the cavity deforming cargo elements 102a–102f and/or carried within cavity deforming vesicle 110 is also deformed, and the so deformed droplet becomes a deformable high-Q optical resonator. Photons resonate within the deformed droplet cavity carried inside cargo elements 102a–102f and/or carried inside within the vesicle 110 within the clathrin cage 106. At critical deformations that tune the Q-value and resonant frequency of the droplet cavity, lasing occurs, and stimulated light emissions from the droplet are released in a highly directional and controlled manner from the droplet and escape from vesicle 110, and or escape from cargo elements 102a–102f, and or escape from cage 106.

The result is a Q-switched ARC droplet nanolaser that provides a room temperature, ultralow-threshold, highly controllable, strongly directional, ultrabright laser light source device that operates at the nanoscale, and also features the capability to store light.

An alternative illustrative embodiment of the ARC nanolaser uses a cavity forming vesicle 110 and/or cavity forming cargo elements 102a–102f located within cage 106, but substitutes the dyed liquid droplet with an "ARC photonic dot", which is comprised of one or more quantum dots contained in the high-Q three-dimensional nanocavity of vesicle 110 or cargo elements 102a–102f. Selectable quantum dot energy level emissions and/or vesicle 110 cavity deformation, and/or cargo elements 102a–102f cavity deformation, precisely excite the whispering gallery modes in the cavity forming vesicle 110 and/or in the cavity forming cargo elements 102a–102f.

At various calculated critical deformations of the cavity forming vesicle 110 and/or the cavity forming cargo elements 102a–102f, and/or at specific quantum dot energy emissions that may also assist in tuning the Q-value and resonant frequency of the ARC photonic dot, lasing occurs and stimulated light emissions from the ARC photonic dot are released in a highly directional and controlled emission manner from the vesicle 110, the cargo elements 102a–102f and/or the cage 106. The Q-switched ARC photonic dot provides a room temperature, ultralow-threshold, highly controllable, ultrabright laser light source device that operates at the nanoscale, and also features the capability to store light.

In another ARC laser embodiment, a droplet ARC nanolaser and a photonic ARC nanolaser are combined to create a hybrid droplet/photonic dot ARC nanolaser.

Optical pumping of the dyed droplet and excitation of the quantum dot is done through methodologies known in the art. Outgoing light from the vesicle 110, cargo elements 102*a*–102*f* and/or cage 106 can be directed and controlled through methodologies also known in the art.

In one illustrative embodiment, highly controllable ARC nanolasers, droplet based and/or photonic-based, are a regulated source of photons for use in quantum computing and quantum cryptography.

In another illustrative embodiment, highly controllable ARC nanolasers, droplet based and/or photonic-based, with broad and continuous tunable wavelength and ultra low threshold are a light source for use in wavelength division multiplexing, optical fiber communications, and free-space optical interconnects.

In one embodiment, highly controllable ARC nanolasers, droplet based and/or photonic-based, with broad and continuous tunable wavelength are a light source for use in ultra bright, ultra low power human- and machine-readable displays.

In another embodiment, highly controllable ARC nanolasers, droplet based and/or photonic-based, are used for light and/or information storage.

Another embodiment of highly controllable ARC nanolasers, droplet based and/or photonic-based, constitutes an ultra bright ultra low power light source for use in medical diagnosis, therapy, and prosthesis, in vivo and/or in vitro.

In another illustrative embodiment, highly controllable ARC nanolasers, droplets based and/or photonic-based, are broad and/or narrow spectrum sensors.

In another illustrative embodiment, highly controllable ARC nanolasers, droplet based and/or photonic-based, utilize solar energy as an excitation and or optical pumping source for use in high efficiency solar cells.

In one embodiment, highly controllable ARC nanolasers, droplet based and/or photonic-based, with strongly directional ultra bright light output are a source of highly steerable and directed photonic energy.

FIG. 2 is a conceptual diagram depicting a basic unit of clathrin, a three-armed pinwheel structure called a triskelion 200. The filamentous portion of a clathrin triskelion leg is formed by a continuous superhelix. Clathrin is composed of three polypeptides, three 190 kDa subunits ("heavy chains") and three 24–27 kDa subunits ("light chains"), which combine to create a distinct three-legged triskelion 200. It is this morphology that allows clathrin to form its unique polyhedral network. The three-arms 202*a*–202*c* extend radially from a hub section 208. Each arm 202*a*–202*c* includes one heavy chain section 204*a*–204*c*, respectively, and one light chain section 206*a*–206*c*, respectively. The heavy chain sections 204*a*–204*c* are relatively flexible and can adopt different geometry's within the clathrin cage 106. In one illustrative embodiment, the clathrin triskelia 200 are biologically engineered to modify and/or enhance the properties of the heavy chain sections 204*a*–204*c*, including the heavy chain terminal domain that provides multiple interaction sites for the variety of adaptor proteins that bind ligands.

In another illustrative embodiment, the clathrin triskelia 200 are biologically engineered to modify and/or enhance the clathrin light chain section 206*a*–206*c* located proximal to the center of clathrin triskelion 200 to accept free radical molecules such as nitroxide molecule spin labels for ESR-based QIP applications. In the case of nitroxide, the molecules are attached to a short molecular tether to clathrin light chain section 206*a*–206*c* by cysteine substitution mutagenesis, followed by reaction of the unique cysteine with a specific molecular spin label.

In another embodiment, no molecular tether is involved and a free radical molecule may be attached directly to cage 106. In another embodiment, a free radical molecule may be attached to receptors 104*a*–140*f*.

Clathrin networks are formed when several triskelia of the type depicted in FIG. 2 associate together to form a lattice or cage 300, as illustrated by FIG. 3. The clathrin cage 300 includes a symmetrical pattern of hexagons 302 and pentagons 304. In the illustrative embodiment, the clathrin cage 106 has icosahedral geometry.

As mentioned above, naturally in vivo occurring clathrin cages 106 assemble around membranes to form vesicles. Referring again to FIG. 1, the adapter molecules 108*a*–108*f* couple clathrin proteins 106*a*–106*f* to receptor molecules 104*a*–104*f* disposed around the periphery of the vesicle 110. According to the illustrative embodiment, the clathrin cage 106 is formed around the vesicle 110 in vitro using synthetic, natural, or mixed lipid monolayers or bilayers and purified receptor 104*a*–104*f* and adapter 108*a*–108*f* molecules. For example, in one illustrative embodiment, the clathrin cage 106 is formed by adding biologically engineered clathrin proteins 106*a*–106*f* and adapter molecules 108*a*–108*f*, such as AP-2 and AP180, to a PIP2-containing lipid monolayer. According to one feature of the invention, the receptor molecules 104*a*–104*f* are biologically engineered to recognize and associate with specific molecules that serve as the cargo elements 102*a*–102*f*. According to another feature, the adapter molecules 108*a*–108*f* are biologically engineered to recognize specific receptor molecules 104*a*–104*f* and couple the receptor molecules 104*a*–104*f* to the clathrin cage 106.

Alternatively, the clathrin cage 106 can be formed in vitro, without the vesicle 110, by changing the pH or ionic strength of the solution in which the clathrin proteins 106*a*–106*f* are located.

Below pH 6.5, purified clathrin triskelions self-assemble in vitro into a polyhedral lattice (cages) without vesicles, but typically only form cages at physiological pH in the presence of stoichiometric quantities of purified AP-1 or AP-2 adaptor molecules or the neuron-specific assembly proteins AP-180 and auxilin. Recombinant hubs, formed from residues 1074–1675 of the clathrin heavy chain, are trimeric structures that reproduce the central portion of the three-legged clathrin triskelion, extending from the vertex to the bend in each leg, comprising the binding sites for clathrin light-chain subunits. Without light-chain subunits, recombinant hubs self-assemble reversibly at physiological pH, while hubs with bound light chains self-assemble below pH 6.5, similar to purified clathrin. Inhibition of hub assembly by light-chain subunits is a key to controlling spontaneous clathrin self-assembly at physiological pH. The mean curvature of baskets (cages without vesicles) is adjustable by the pH level and by other environmental conditions. As can be deduced from the formation of the microcages, a clathrin network can have such a pH-controlled curvature, even in the absence of a membrane bilayer. In addition, a conserved negatively charged sequence of three residues (23–25) in the clathrin light-chain subunits regulates the pH dependence of hub assembly. Also, two classes of salt bridge (high affinity and low affinity bridges) play a dominant role in driving clathrin assembly. Basket closure depends on the presence of TDD domains (terminal and distal domains). A connection between the proximal and distal domains is not required for curvature, and the TDD themselves can orient the assembling hubs in a favorable angle for polyhedron formation.

Figure 4:
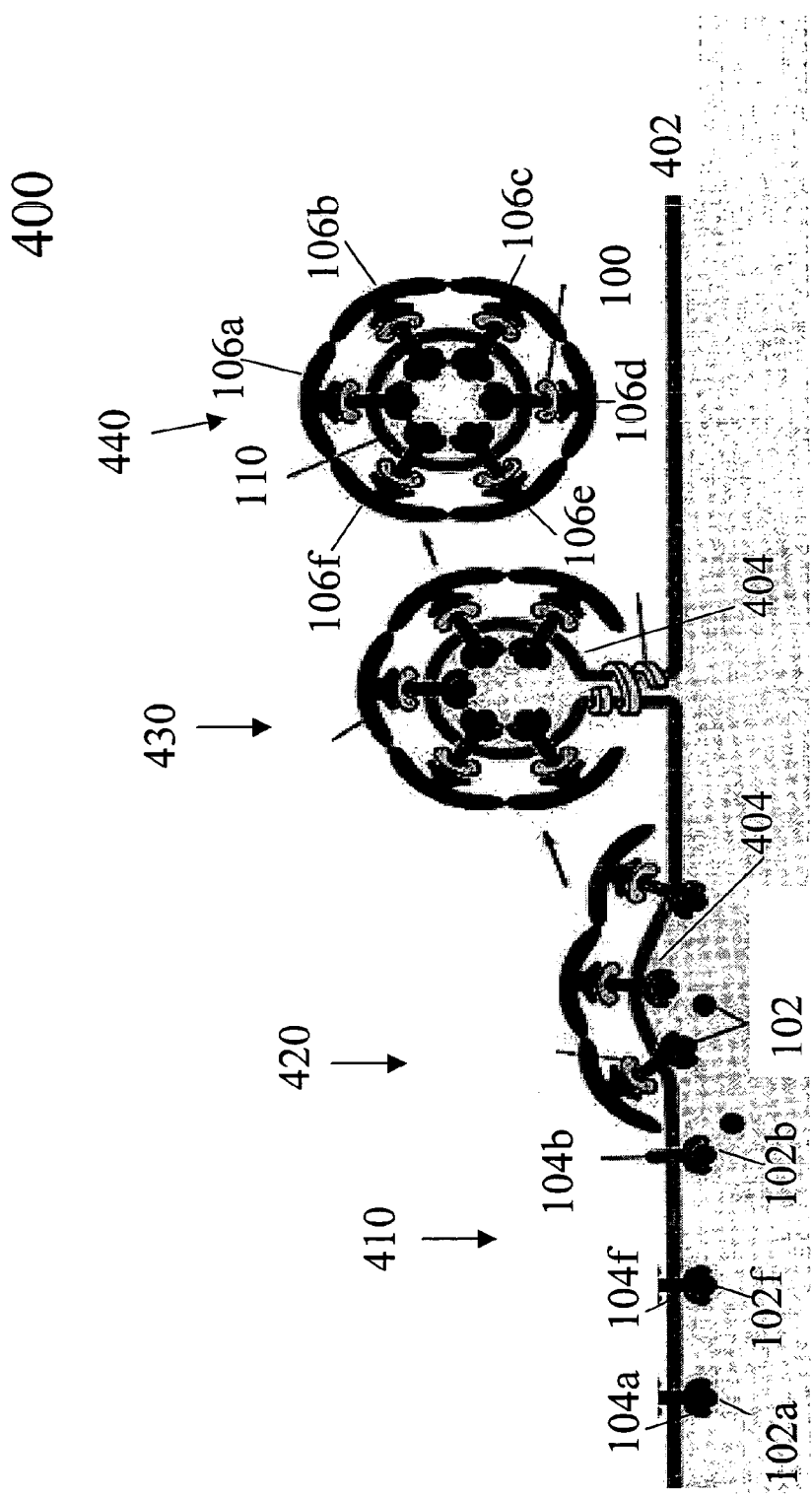
FIG. 4 is a flow diagram depicting conceptually the formation of a QIP element in vitro according to an illustrative embodiment of the invention.

FIG. 4 is a flow diagram 400 depicting, conceptually, the formation of a QIP element 100 according to an illustrative embodiment of the invention. The process by which the clathrin molecules 106a–106f obtain cargo molecules 102a–102f in vivo is known as endocytosis. The endocytosis process begins when proteins bound to receptors accumulate in coated pits, which are specialized regions of the membrane where it is indented and coated on its cytoplasmic side with a bristle-like coat composed of two proteins: clathrin and protein adapters. Referring to FIGS. 1 and 4, in the case where a vesicle 110 is desired, the cargo molecules 102a–102f are initially located behind a membrane, such as a cytosol membrane 402. As shown at 410, the receptor molecules, such as the receptor molecules 104a, 104b and 104f, bond with the cargo molecules, such as the cargo molecules 102a, 102b and 102f, respectively, through the membrane 402. As shown at 420, the clathrin molecules, such as the clathrin molecules 106a, 106b and 106f then bond through the adaptor molecules, such as the adaptor molecules 108a, 108b and 108f, respectively, to the receptor molecules, such as the receptor molecules 104a, 104b and 104f, respectively, to begin to form a clathrin coated vesicle (CCV) with icosahedral symmetry. Regulatory processes within membrane 402 cause clathrin bud 404 to form at 420. As shown at 430 and 440, after forming completely around the bud 404, the clathrin cage 106 pinches off (scissions) from the membrane 402 leaving it with the cargo molecules 102a–102f inside the vesicle 110. After excision, the bud 404 has evolved into clathrin cage 106, a complete CCV with a symmetric icosahedral structure.

The heat shock cognate protein, hsc70, helps to regulate the endocytosis aftermath of CCV uncoating and disassembly. In cells overexpressing ATPase-deficient hsc70 mutants, uncoating of CCVs is inhibited in vivo. In a preferred embodiment, an over expression of ATPase-deficient hsc70 mutants may be applied and hsc70 mutants additionally modified via bioengineering techniques to inhibit both CCV and non-vesicle cage disassembly, thereby maintaining CCV and clathrin cage integrity in the invention over prolonged periods of time in vivo and in vitro.

According to one illustrative embodiment, the above CCV assembly process is carried out by preparing clathrin-coated vesicles 110 for incorporation of QIP cargo elements, such as the cargo elements 102a–102f, from cytosolic preparations essentially as described in Takei, et al., Cell, 94: 131–141 (1998), incorporated by reference herein. Liposomes are prepared as described in Reeves, et al., J. Cell Physiol., 73: 49–60 (1969), incorporated by reference herein. Essentially, lipids are solubilized in a 1:2 mixture of chloroform and methanol, and dried in a rotary evaporator. The preparation is rehydrated in a stream of water-saturated nitrogen for twenty minutes. Lipids are then placed in a flask with gently degassed 0.3M sucrose. The flask is flushed with nitrogen, sealed, and left undisturbed for two hours at 37 degrees Celsius. Liposomes are then recovered by centrifugation at 12,000×g for ten minutes and resuspended in cytosolic buffer prior to incubation.

Cytosolic preparations are made by any convenient method. Numerous methods are described in the art. See, e.g., Huttner, et al., J. Cell Biol., 96: 1374–1388 (1983), incorporated by reference herein. Essentially, viable cells are collected by centrifugation and resuspended in hypotonic lysis buffer. Membranes are disrupted by homogenization, and the cytosolic fraction is collected after pelleting membrane debris. Briefly, cells obtained from culture are transferred to hypotonic lysis buffer (100 mM HEPES (pH7.9), 15 mM MgCl2, 100 mM KCl, 0.1M DTT) and centrifuged. The resulting pellet is resuspended in phosphate buffered saline and centrifuged. The supernatant is decanted. A volume of lysis buffer is then added that is about five times the pellet volume. The pellet is gently resuspended and placed on ice in lysis buffer for 15 minutes. The suspension is then centrifuged for 15 minutes at 420×g. The supernatant is removed and discarded and the pellet is resuspended in a volume of lysis buffer equal to twice the pellet volume. Cells are disrupted by ejection through a syringe, and the disrupted cells suspension is centrifuged at 10,000×g for 20 minutes. The resulting supernatant is the cytosolic fraction.

Next, clathrin coated proteins are extracted from clathrin-coated vesicles 110 obtained from organic tissue. According to one illustrative embodiment, bovine brain tissue is used. Coat protein is extracted from coated vesicles in a buffer containing 0.8M Tris-HCl (pH 7.4), 2 mM EGTA, 0.03% sodium azide, 0.5 mM DTT, and 1 mM PMSF for fifteen minutes at room temperature. The preparation is then centrifuged at 100,000×g for one hour at room temperature to produce a supernatant containing soluble coat protein. The isolated proteins are used directly or frozen in liquid nitrogen at −70 degrees Celsius.

Clathrin-coated vesicles 110 are generated by incubation of liposomes (1 mg/ml) in 1 ml of cytosolic buffer (25 mM HEPES-KOH (pH 7.4), 25 mM KCl, 2.5 mM magnesium acetate, 150 mM K-glutamate) with 6 mg/ml cytosol, 0.5 mg/ml coat proteins with ATP (2 mM final concentration) and GTPS (200 uM final concentration). The resulting clathrin-coated vesicles 110 can be visualized under electron microscopy as described below.

According to one illustrative embodiment, recombinant clathrin formation may be achieved in the following manner. Stoichiometric quantities of adaptor element 206 proteins AP-1 and AP-2 are required for clathrin self-assembly at physiological pH. However, in vitro clathrin self-assembly occurs spontaneously below about pH 6.5. Recombinant terminal and distal domain fragments are produced and combined with recombinant-produced hub fragments in assembly buffer as described below in order to induce formation of closed clathrin cages, such as the cage 106, for use in the invention.

Bovine clathrin heavy chain cDNA encoding heavy chain amino acids 1-1074 (SEQ ID NO: 1) is cloned into the pET23d vector (Novagen) between the NcoI(234) and XhoI (158) sites. Expression of the cloned sequence results in a terminal and distal domain fragments having a C-terminal polyhistidine tag. Hub fragments corresponding to amino acids 1074–1675 (SEQ ID NO: 2) are cloned into vector pET15b (Novagen) between the BamHI(319) and XhoI (324) sites. Expression of the hub fragments produces the proximal leg domain and central trimerization domain of the clathrin hub with an N-terminal polyhistidine tag. Vectors containing the heavy chain and hub domains are expressed in E. coli by induction with 0.8 mM isopropyl-B-D-thiogalactopyranoside for 3 hours at 30 degrees Celsius. Expressed proteins are purified from bacterial lysate in binding buffer (50 mM Tris-HCl (pH7.9), 0.5M NaCl, 5 mM imidazole) in a nickel affinity resin using the polyhistidine tag. Proteins are eluted with 100 mM EDTA and dialyzed against 50 mM Tris-HCl (pH7.9). Hub fragments are further purified using size exclusion chromatography on a Superose 6 column (Pharmacia).

Clathrin assembly reactions are performed using expressed heavy chain and hub fragments by overnight dialysis at 4 degrees Celsius in assembly buffer (100 mM 2-(N-morpholino) ethanesulfonic acid, pH 6.7, 0.5 mM MgCl2, 1 mM EGTA, 1 MM Tris(2-carboxyethyl)-phosphine hydrochloride, 3 mM CaCl2. Assembly reactions are centrifuged for 5 minutes at 12,000 rpm. The supernatant is then centrifuged for 45 minutes at 45,000 rpm (100,000×g). The pellets are resuspended in assembly buffer, and protein composition is determined on SDS-PAGE. The efficiency of cage 106 formation can be determined by electron microscopy by diluting assembly reactions 1:5 in 10 mM Tris pH7.9, and placing aliquots on a glow-discharged carbon-coated grid, using 1% uranyl acetate as the stain. Cage 106 formation is assessed by counting the numbers of cages 106 having closed, defined edges and visible hexagonal/pentagonal lattice structure.

As mentioned above, the cargo elements $102a–102f$ may include various QIP and/or non-QIP cargo elements, in any combination. By way of example, in some illustrative embodiments, the non-qubit cargo elements $102a–102f$ include one or more nanoscale passive linear or nonlinear optic components and/or particle detectors, which when used in conjunction with various other QIP elements, including some that utilize qubits, are sufficient for implementing reliable quantum algorithms on a QIP platform.

In another illustrative embodiment, the cargo elements $102a–102f$ include one or more photonic dots. The one or more photonic dots may be one or more quantum dots contained in three-dimensional nanocavities formed by cargo elements $102a–102f$.

In further illustrative embodiments, free-floating qubits may be carried in cavity forming, non-permeable, cargo elements $102a–102f$ that contain a fluid or vapor, and/or be carried within a cavity forming, non-permeable vesicle 110 filled with a fluid or a vapor within cage 106, which free-floating qubits, for example, may be atomic ensembles for spin-based QIP. In further illustrative embodiments, the cargo elements $102a–102f$ include one or more asymmetric resonant cavity nanolasers.

Preferably, some QIP elements include cargo, such as a molecule having an unpaired electron (e.g., a free radical, such as nitroxide), a transition metal ion, which can be found in the active centers of many proteins (metalloproteins), or a material having any defect that produces an unpaired electron. Non-QIP cargo elements may include, for example and without limitation, organic cosmetics, pharmaceuticals, biologicals, radioactive agents, magnetic iron oxide nanoparticles, or other substances, and also may include nanoscale biosensors, diagnostic systems, or other nano-devices for in vivo delivery of targeted therapy to combat diseases, such as cancer. In vivo delivery of such nano-biomedical systems may utilize a variety of techniques, like degradable coatings and nanoscale electro-mechanical systems, which are capable of being harmlessly dissolved or harmlessly passed through the body. Other non-QIP biomedical cargo elements may include, for example, intelligent nano-prostheses that supplement or enhance cell, tissue, or organ functioning, thereby providing them with augmented capabilities. Some or all such non-qubit cargo may operate under the control and influence of various other QIP elements, and comprise another type of QIP platform.

In operation, the self-assembling proteins that make up the QIP element 106 naturally shield the qubits contained within the cage 106 from electron charge transfers and prevent distortion of the cage 106. Such charge transfer and structure distortion would make cage 106 unsuitable for quantum computation because rapid decoherence would occur. Thus, the clathrin cage 106 shields the qubit and non-qubit cargo, consequently reducing the tendency of the system towards decoherence. The shielding properties of the cage 106 also inhibit adverse charge transfer interactions between various cages and their respective qubit and non-qubit cargo.

According to a further feature, the protein receptors $104a–104f$ shield cargo elements $102a–102f$ in the same clathrin cage 106 from interacting with each other. According to a further feature, the protein adaptors $108a–108f$ shield cargo elements $102a–102f$ in the same clathrin cage 106 from interacting with each other. According to another feature, the vesicle 110 shields cargo elements within vesicle 110 in the same clathrin cage 106 from interacting with each other. As another feature, the natural shielding capabilities of the cage 106 allow for direct molecular or chemical bonding of suitable qubit and non-qubit cargo elements to the cage 106 without causing distortion of the cage 106, as exemplified by the non-distorting bonding of the adaptors $108a-108f$ and the receptors $104a–104f$ to the cage 106.

During processing operations, the cargo elements $102a–102f$ can be made to interact with, for example, an externally applied magnetic field. However, since the clathrin cage 106 is electrically neutral, only minimal (e.g., no) structural distortion of the clathrin cage 106 occurs in the presence of the magnetic field. Therefore, using the clathrin cage 106 to capture cargo elements $102a–102f$ protects and extends quantum coherence.

Figure 5:
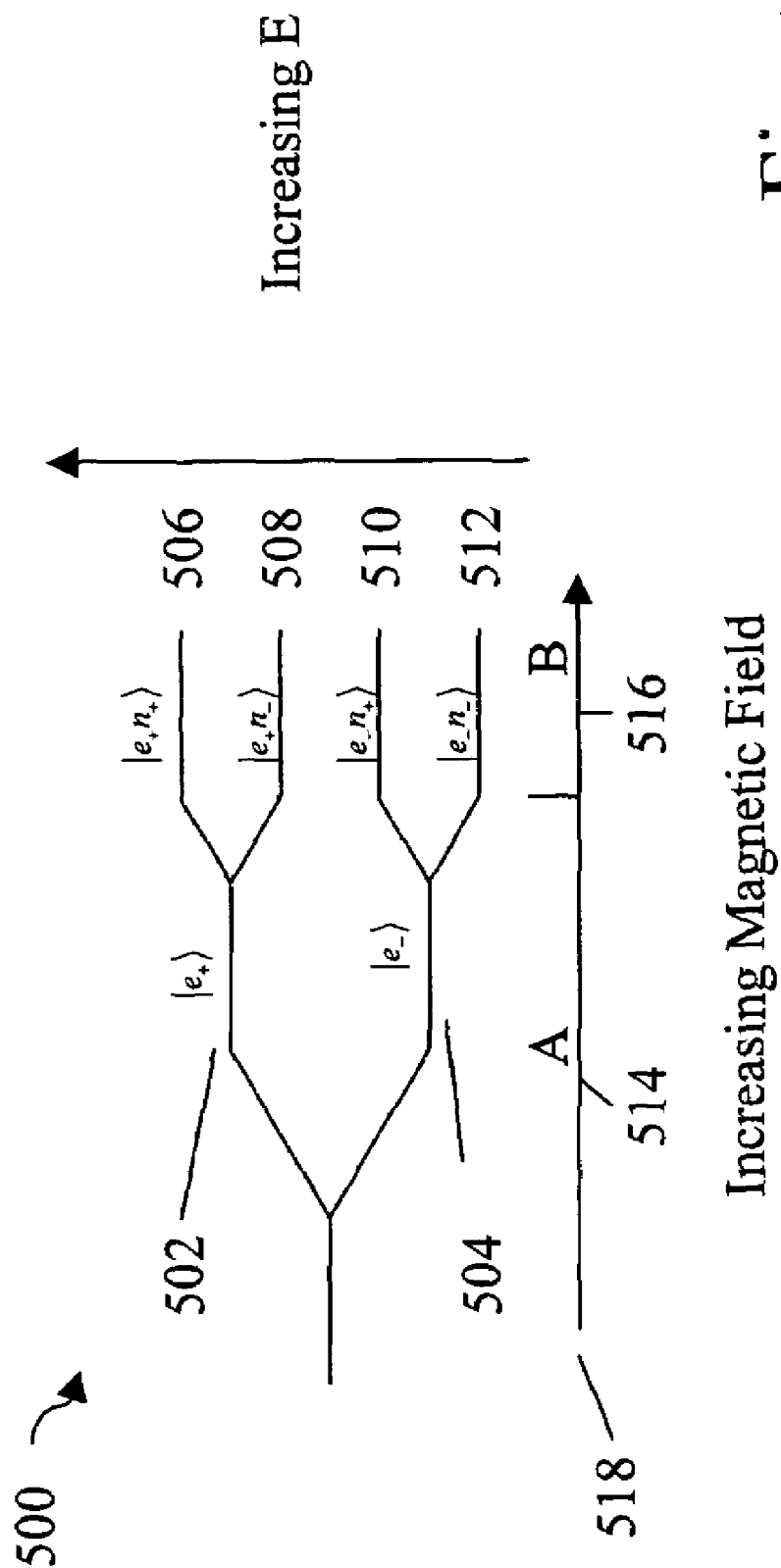
FIG. 5 is an exemplary energy level diagram illustrating the energy levels associated with a hyperfine interaction between electron and nuclear spin in the presence of magnetic fields.

FIG. 5 is an exemplary energy level diagram 500 illustrating the energy levels associated with a hyperfine interaction between electron and nuclear spin in the presence of magnetic fields of the type used to program information into and read information from the illustrative QIP element of FIG. 1. The hyperfine interaction is a strictly quantum mechanical phenomenon. In an atom, the electron possesses an intrinsic quantum mechanical quantity known as spin. The nucleus of an atom also possesses spin. Intrinsic spin tends to generate a spin magnetic moment that is capable of interacting with other magnetic moments and fields. Generally, the spin magnetic moment of the nucleus does not interact with the spin magnetic moment of the electron. However, in the presence of a strong magnetic field, the spin magnetic moments of the electron and nucleus become coupled and interact.

When an external magnetic field 518 is applied to an atom, the electron spin may either be parallel or anti-parallel with the field or askew to the field. Parallelity is referred to as the "spin up" state and is denoted by $e_+$ 502. Anti-parallelity is referred to as the "spin down" state and is denoted by $e_-$ 504. Generally, the spin down state represents quantum logical "0" state, |0>, and the spin up state represents quantum logical "1" state |1>. In the illustrative embodiment, a single qubit is represented by electron spin. In one illustrative embodiment, the electron spin interaction is used to program and read QIP elements using electron spin resonance techniques (ESR). In such an illustrative electron spin-based quantum computer embodiment, the spin sites within the self-assembling and insulative protein cage 106 may be physically manipulated and replicated in numbers, may possess inter-site interactions, and are isolated from their environment.

The same magnetic properties apply to nuclear spin with $n_+$ referring to nuclear spin up 506 and 510, and thus a quantum logical |1> and $n_-$ referring to nuclear spin down 508 and 512, and thus, a quantum logical |0>. In another illustrative embodiment, the nuclear spin interaction is used to program and read QIP elements using nuclear magnetic resonance (NMR). Additionally, NMR may be combined with other QIP techniques, such as ENDOR, which combines the best aspects of ESR and NMR, to yield high sensitivity and nuclear selectivity, respectively.

A hyperfine interaction occurs in magnetic fields of strength greater than that of region B 516. For magnetic fields less than that of region B, i.e., region A 514, two one-qubit states may exist, illustratively named e+ 502 or e− 504 corresponding to the spin of the electron. These two states may be generalized beyond electron spin to any information that may be used for quantum information processing or as a qubit, i.e., spin or energy.

By way of example, if a qubit is initially in some state representing |0> 504, a NOT operation can be performed by shining a pulse of light of appropriate wavelength on a qubit atom to force an electron to change energy levels. Thus, an electron initially in the ground state absorbs energy from the light pulse and is excited to the higher energy state. The wavelength of the applied light pulse must at least match the energy difference between the two energy levels separating the logic states (i.e., between the ground state and the excited state of the nitroxide) as governed by Planck's quantization law.

$$E = \frac{hc}{\lambda}$$

where

E=energy difference between energy levels of orthogonal quantum logic states
h=Planck's constant
c=the speed of light, and
λ=wavelength of the applied pulse.

If the pulse exceeds the energy required for excitation, the extra energy is emitted as a photon after the electron reaches the higher energy level, i.e., |1>.

In a further illustrative embodiment, an applied magnetic field interacts with the electron spin, but not with the nuclear spin, i.e., in the A region 514. This configuration gives rise to two one-qubit states using spin |0> 502, |1> 504. The NOT operation in this configuration involves changing the direction of the applied magnetic field 518. In one illustrative embodiment, the electron is excited using pulses of electromagnetic radiation while maintaining its spin configuration. The source of the electromagnetic radiation may be, for example, an ordinary lamp, an LED, a time-varying magnetic field generator, a laser, or an electromagnetic field generator. In the illustrative embodiment, the electromagnetic source acts as a writing element.

The Hamiltonian that represents the hyperfine interaction between the electron and nuclear spin appears in Dowling, J., Bowden, C., and Hotaling, S., *Electron-Nuclear-Double-Resonance Quantum Computer* (on file with inventor) incorporated by reference herein. The relevant spin interaction Hamiltonian is as follows:

$$H = g\mu_e H_0 S_e^z + g\mu_N H_0 S_N^z + J S_e^z S_N^z + H(t)$$

where g=gyromagnetic ratio,
$\mu_e$=magnetic moment of the electron,
$S_e^z$=intrinsic spin angular momentum tensor of the electron in the z direction,
$\mu_N$=magnetic moment of the nucleus,
$S_N^z$=intrinsic spin angular momentum tensor of the nucleus in the z direction,
$H_0$=the DC magnetic field, and
H(t)=the time-dependent spectroscopic protocol.

For resonance purposes:

$H(t) = Ae^{-i\omega t} + Be^{i\omega t}$ where A and B represent complex amplitudes, e represents the Euler function, i represents $\sqrt{-1}$, ω represents the resonant frequency of the nucleus and t represents time. According to the illustrative embodiment, H(t) is a pulse of a sinusoidally varying magnetic field designed to flip between two of the energy eigenstates 506, 508, 510 and 512 representing a two-qubit state.

The interaction between the electron spin magnetic moment, nuclear spin magnetic moment, and the external magnetic field 518 gives rise to a four distinct, discrete energy levels 506, 508, 510 and 512. Each of the four energy levels refers to a two-qubit state embodying one contribution of nuclear spin and one contribution of electron spin, namely |00> 512, |01> 510, |10> 508, |11> 506. A hyperfine interaction gives rise to electron nuclear double resonance (ENDOR) computation techniques. According to one illustrative embodiment of the invention, ENDOR is used to program and read information from QIP elements such as the QIP element 100. According to another embodiment, room temperature EPR and ENDOR techniques known in the art for performing in vivo spin probe studies may be adapted for the invention.

Figure 2:
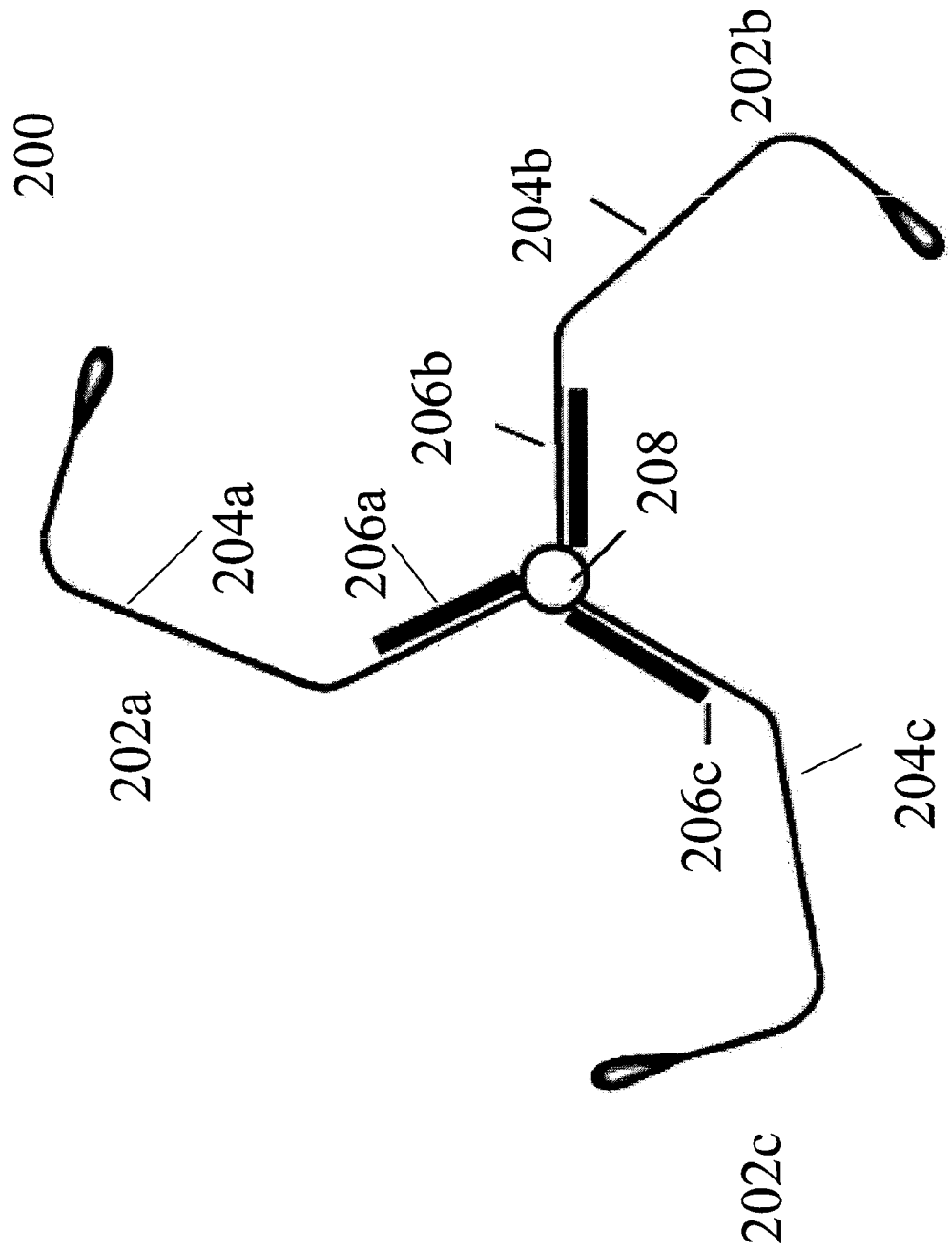
FIG. 2 is a conceptual diagram depicting a clathrin triskelion of the type employed in an illustrative embodiment of the invention.
Figure 3:
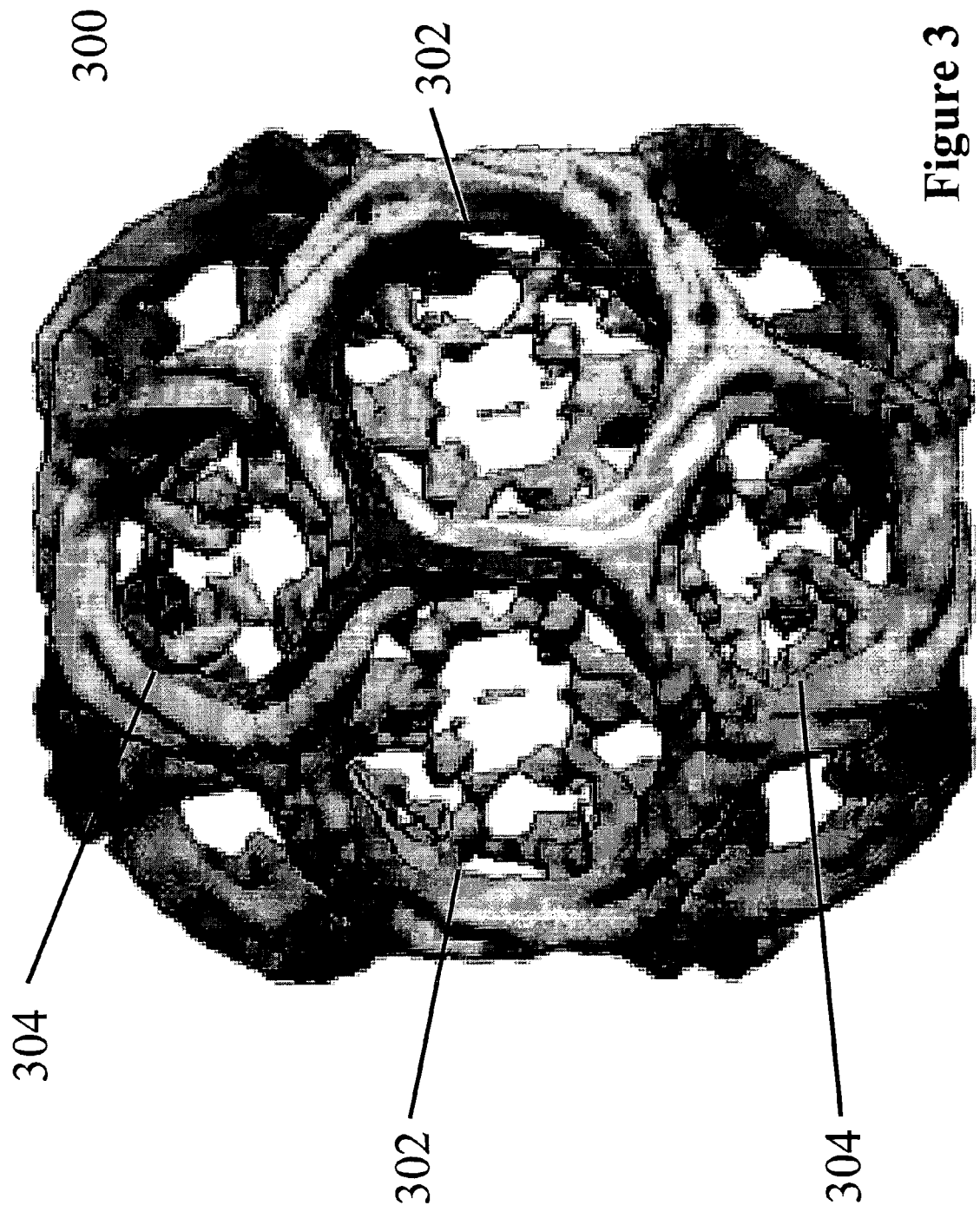
FIG. 3 is a computer generated frontal view of an actual clathrin protein cage, formed according to an illustrative embodiment of the invention.
Figure 6:
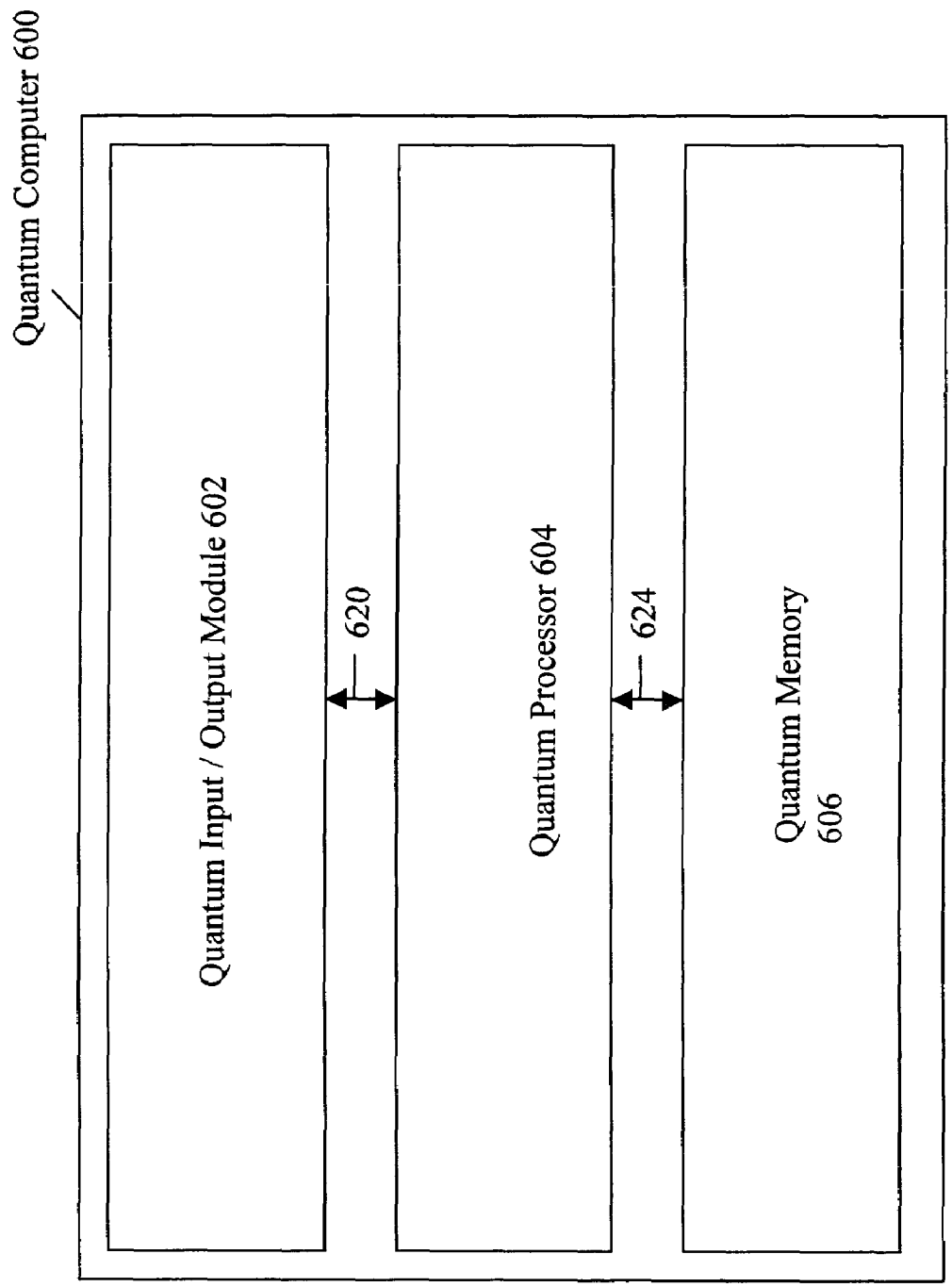
FIG. 6 is a simplified block diagram of a quantum computer employing protein-based QIP elements according to an illustrative embodiment of the invention.

FIG. 6 is a simplified block diagram of a quantum computer 600 employing protein-based QIP elements of the type shown in FIG. 1 at 100. The quantum computer 600 includes components analogous to those of a classical computer, such as a quantum input/output (I/O) module 602, a quantum processor 604, and quantum memory 606. These components use the illustrative self-assembling protein molecules of FIG. 2 as a building block. As shown, the quantum processor 604 includes an internal quantum I/O module 602 and/or an internal quantum memory 606. It should be noted that the boundaries between the components of FIG. 6 are conceptual in nature and any of the components may be located within any of the other components or external to the quantum computer 600 without deviating from the scope of the invention. The illustrative quantum I/O module 602, the quantum processor 604, and the quantum memory 606 communicate with one another over quantum wires 620 and 624. An illustrative embodiment of such quantum wires are described in more detail below with respect to FIG. 17.

Figure 7:
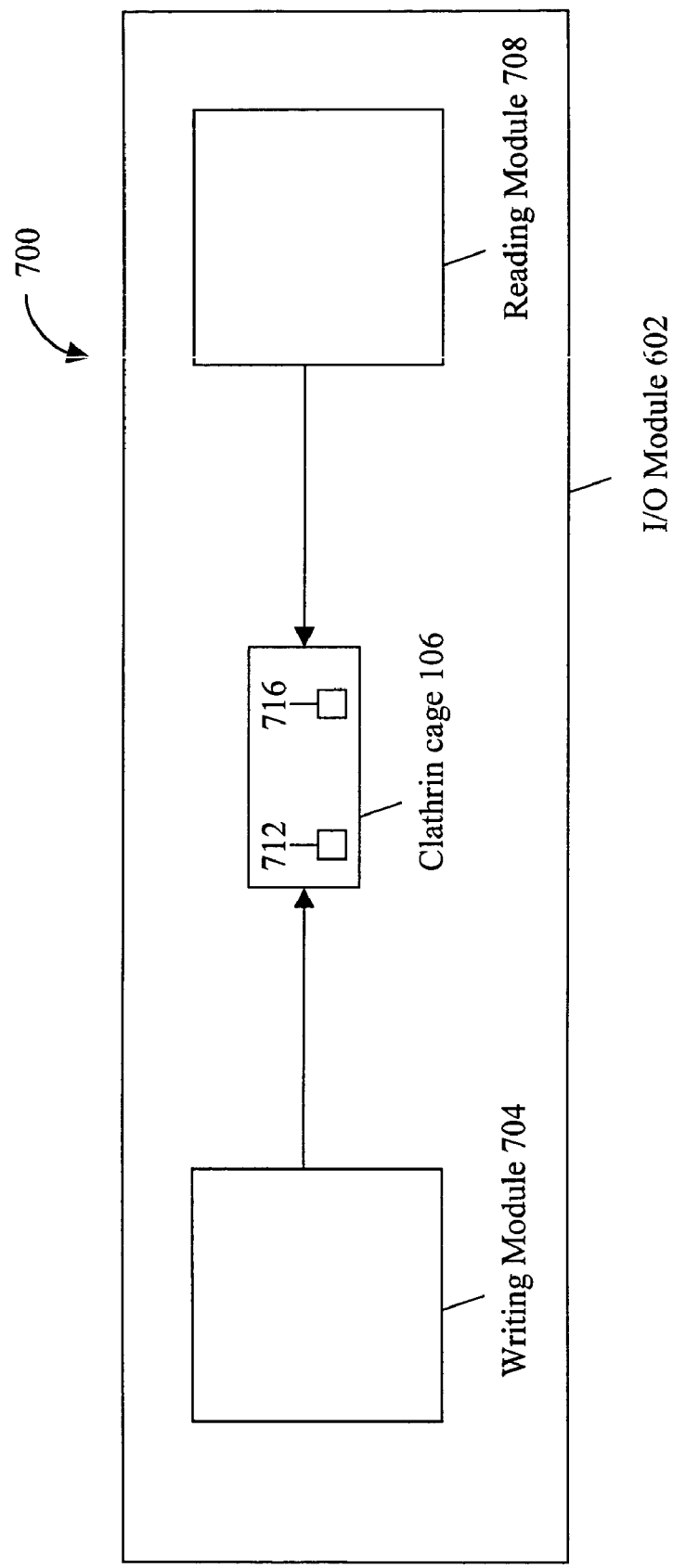
FIG. 7 is a block diagram depicting an illustrative embodiment of the quantum input/output module of FIG. 6.

FIG. 7 is a block diagram depicting an illustrative embodiment of the quantum input/output (I/O) module 602 of FIG. 6. The quantum I/O module 602 includes a writing module 704 and a reading module 708. The writing module 704 can write a state to a qubit 712 such as the cargo elements 102a–102f in the protein cage 106. Thus, in one embodiment, the writing module 704 changes the state of a qubit 712 from a |0> to a |1>. As described above, the writing module 704 can be a source of electromagnetic radiation. In some illustrative embodiments, the writing module 704 initializes the state of a qubit 712 within a QIP element 100 by an optical pumping approach.

In another illustrative embodiment, the writing module 704 initializes the state of a qubit 712 within the protein cage 106 by ESR techniques. ESR detects transitions of unpaired electrons as observed in a magnetic field. In one preferred embodiment, the unpaired electron is a free radical molecule, such as nitroxide. The intrinsic spin magnetic moment of the electron interacts with the magnetic field to establish two distinct energy levels. The energy levels emit radiation, which can be used to observed spectroscopic absorptions by methodologies well-known in the art.

In an alternative illustrative embodiment, the writing module 704 initializes the state of a qubit 712 within the protein cage 106 by NMR techniques. NMR may occur in classical fluids as disclosed by Gershenfeld & Huang, incorporated herein by reference. Gershenfeld, N. and Chuang, L., *Quantum Computing with Molecules*, Scientific American (June 1998). Application of a magnetic field B, such as the magnetic field 518 of FIG. 5, tends to create an imbalance in spin alignments of nuclei. In one illustrative embodiment, a time-varying magnetic field is imposed at the resonant frequency of the nucleus involved. The imposition of this frequency causes nuclei to spin-flip. In some embodiments, imposition of the time-varying magnetic field acts as the writing module 704.

In a further illustrative embodiment, the writing module 704 initializes the state of a qubit 712 within the protein cage 106 by ENDOR techniques. ENDOR combines the best aspects of ESR and NMR, namely high sensitivity and nuclear selectivity, respectively. Optionally, ENDOR is performed by establishing a maximum magnetic field 518 value at which ESR signals occur, known as the ESR absorption signal. Next, an electromagnetic radiation source saturates the electrons with high power microwaves which causes electron heating. To mitigate the heating, and in some embodiments to maintain the operation at room or near room temperature, a sweeping time-varying radio frequency signal sweeps the configuration.

RF does not possess sufficient intensity to drive NMR, thus, in some illustrative embodiments, an RF amplifier amplifies the RF signal sufficiently to drive NMR while cooling the electrons. In one illustrative embodiment, the RF signal is produced by a laser.

The reading module 708 is a quantum device that can measure the state of either qubit 712 or 716. The reading module 708 also may report the measurement. The reading module 708 measures the state of an unknown qubit 712 directly. Preferably, the reading module 708 measures the state of qubits 712 or 716 in a non-destructive manner (i.e., does not disturb the state of the qubit 712 or 716 if the qubit 712 or 716 was initially in state |0> or state |1> (and not in a superposition state)) according to a method depicted in and described below with respect to FIG. 9. Although shown with two qubits 712 and 716, the protein cage 106 may have any number of qubits that the reading module 708 can measure. The reading module 708 may also use quantum jump or electron shelving measurement techniques to measure the final state of the qubit 716.

Figure 8:
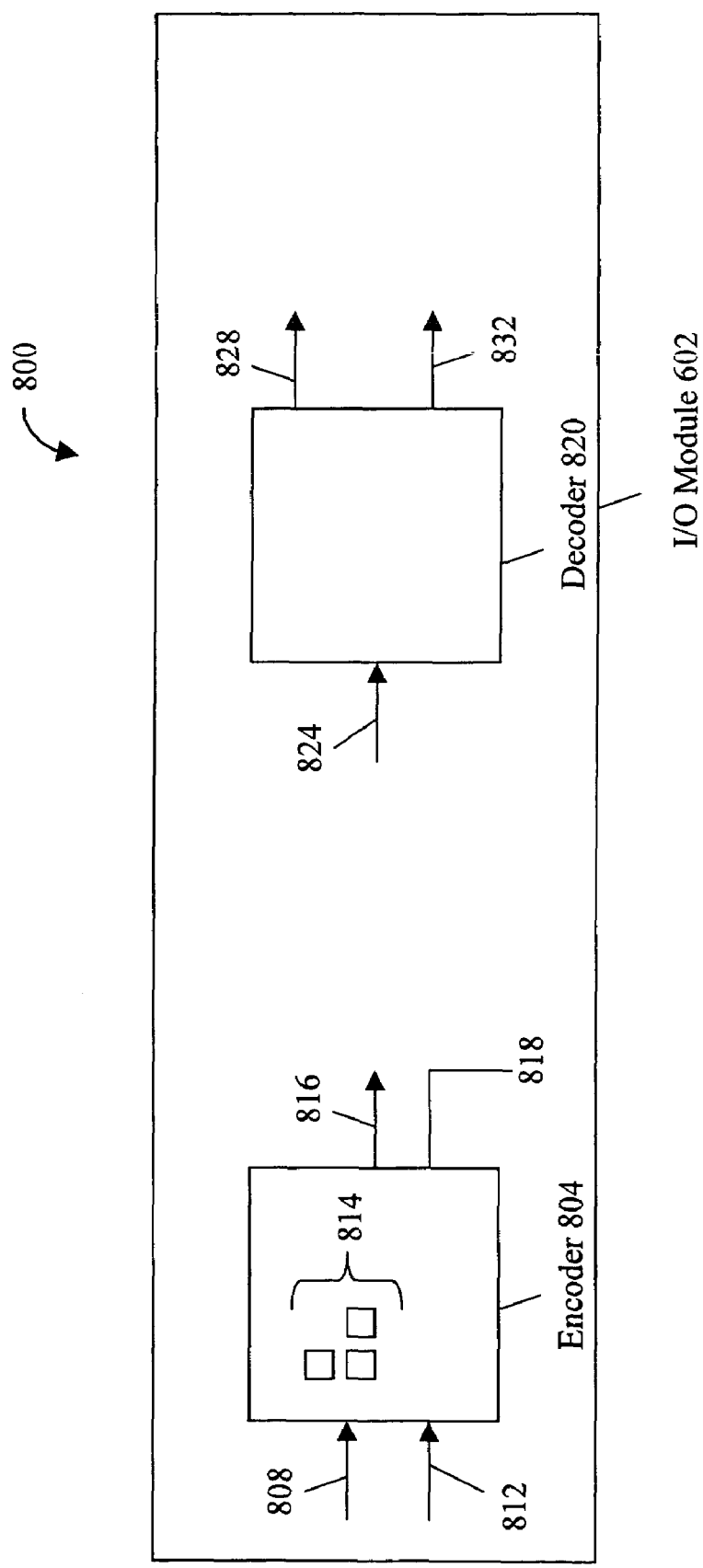
FIG. 8 is a block diagram depicting an exemplary encoder and decoder of the type employed by an input/output module of FIG. 6.

FIG. 8 is a block diagram depicting an exemplary encoder and decoder of the type employed by the illustrative input/output module 602 of FIG. 6. In one illustrative embodiment, the I/O module 602 can also perform quantum error correction. According to the illustrative embodiment, the invention employs the quantum error correction method depicted in and discussed below with respect to FIG. 9. Quantum error correction prevents significant and serious propagation of errors through the computing process. The error correction codes protect against qubit and phase errors, while allowing measurements to determine information about the error that occurred and nothing about the encoded data (to preserve its state). In one illustrative embodiment, the quantum error correction is performed as disclosed in Preskill incorporated herein by reference. Preskill, J., *Reliable Quantum Computers*, quant-ph/9705031 (1997).

The encoder 804 receives an input number of qubits 808 as input and also receives an input number of ancilla qubits 812. The ancilla qubits 812 are scratch qubits, coded to an initial state |0>. The encoder 804 uses a plurality of encoding qubits 814 to encode the input number of qubits 808. In one illustrative embodiment, the number of encoding qubits 814 employed is a predetermined number. In an alternative illustrative embodiment, the number of encoding qubits 814 employed varies depending on the input number of qubits 808. The encoder 804 outputs the encoded qubits 816. In one illustrative embodiment, the encoder 804 includes a series of quantum gates. According to one feature, the encoding is checked by a measurement qubit or plurality of measurement qubits 818. In an alternative illustrative embodiment, a plurality of encoders 804 repeat the operation using the output qubits 816 as input qubits 808. In such an embodiment, sequences of encoders 804 and decoders 820 form quantum error correction elements.

A decoder 820 receives an encoded input 824 (e.g., the encoded qubits 816). The encoded input 824 is an encoded n-qubit state and outputs k qubits 828 together with n-k qubits 832, which, with high probability, specify which error occurred. In one illustrative embodiment, the decoded output 828 represents the output of the QIP element 100.

Figure 9:
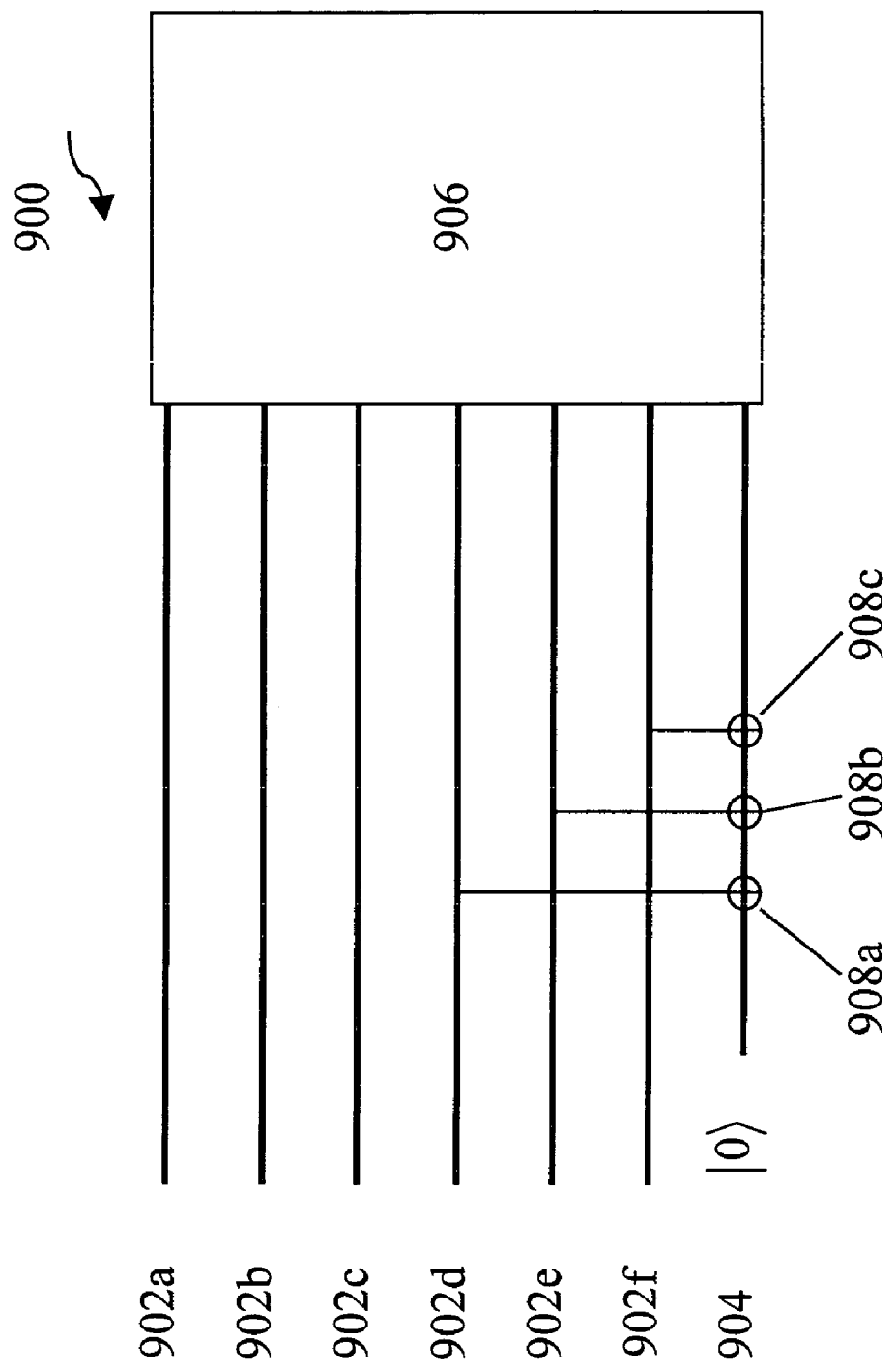
FIG. 9 is a schematic diagram illustrating a logic arrangement for nondestructively measuring a qubit.

FIG. 9 is a schematic diagram illustrating a logic arrangement 900 for nondestructively measuring a qubit. According to the illustrative embodiment, the logic arrangement 900 is used to measure the output of a QIP element 100. In another illustrative embodiment, the logic arrangement 900 is used for quantum error correction. Nondestructive measurement of a qubit requires coherence, and rather than being directly measured, the state of the qubit is inferred from the state of an entangled qubit.

In the illustrative embodiment, a plurality of qubits 902a–902f represent quantum inputs, e.g., qubits. An additional qubit 904 serves as the ancilla qubit. Measurement of the ancilla qubit allows an inference into the state of the unmeasured qubits 902a–902f. In one embodiment, the state of the input qubits 902a–902f after the measurement represents an output 906. For example, in the XOR gate configuration depicted below with respect to FIG. 11, a quantum logic gate uses two qubits for input qubits and includes two qubits as output qubits. Consequently, one of the two input qubits remains unchanged after the quantum logic operation, XOR, is performed. In one embodiment, the ancilla qubit contains a plurality of quantum XOR gates 908a–908c. The operator notation for an XOR gate 908 is ⊕.

Figure 10:
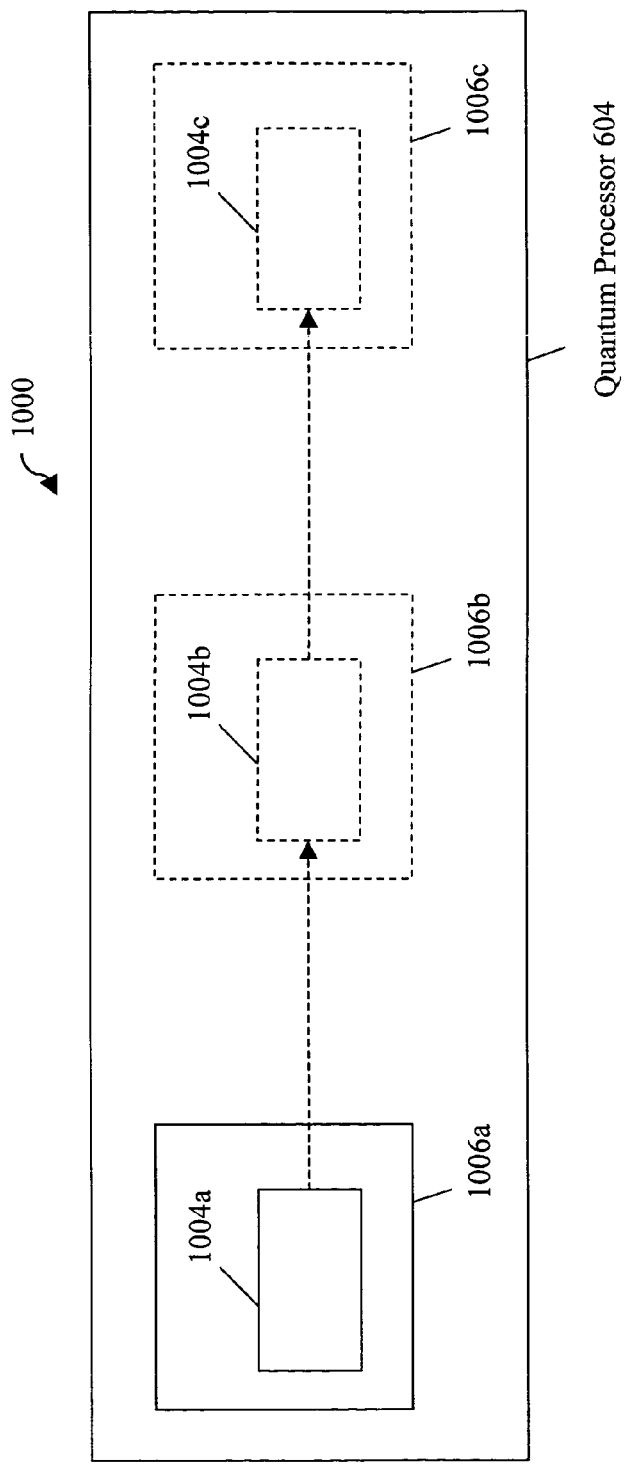
FIG. 10 is a block diagram depicting an illustrative embodiment of the quantum processor of FIG. 6.

FIG. 10 is a conceptual block diagram depicting an illustrative embodiment of the quantum processor of FIG. 6. The quantum gates 1004a–1004c enable the quantum processor 604 to perform quantum computation. Each of the quantum gates 1004a–1004c is located within a respective QIP element 1006a–1006c of the type depicted at 100 of FIG. 1. Although each quantum gate 1004 is illustrated as being located within a respective QIP element, 1006a–1006c, any number of the quantum gates 1004a–1004c may be located within any number of QIP elements 1006a–1006c. For instance, any or all of the quantum gates 1004a–1004c of the quantum processor 604 may be located within a single QIP element 1006a as shown in FIG. 1.

In one embodiment, chains of ordered sequences of QIP elements 1006a–1006c form the quantum computer 600. The QIP elements 1006a–1006c may all have the same fillings (e.g., four qubits 102a–102d of nitroxide and fifteen non-qubits) or may have different fillings (e.g., the first QIP element 1006a has one qubit 102a and the second QIP element 1006b has four or more qubits 102a–102d). In one illustrative embodiment, a clathrin chain is created via a molecular bridge group. To align the QIP elements 1006a–1006c with respect to one another and with respect to an external magnetic field, the QIP elements 1006a–1006c may be embedded into various materials, such as liquid crystal. Empty cage (non-cargo carrying) 106 QIP elements may also be used to self-align cargo carrying QIP elements 1006a–1006c, and the entire QIP element assembly may be embedded in another material.

In one illustrative embodiment, unitary operations on the qubits 102a–102f are quantum logic gates. In one embodiment, a single bit quantum gate 1004a–1004c may be the rotation of a single qubit 102a in the clathrin cage 106. For example, if a qubit 102a evolves as orthogonal state |0>→|0> and orthogonal state |1>→$e^{i\omega t}$|1>, then after time t the operation, or 'gate'

$$P(\theta) = \begin{pmatrix} 1 & 0 \\ 0 & e^{\theta} \end{pmatrix}$$

has been applied to the qubit 102a, where θ=ωt with ω representing frequency and t representing time, e represents the exponential function, and P(θ) is a rotation matrix representing the gate.

The quantum processor 604 can perform several quantum transforms with a quantum gate 1004 within a QIP element 100. Examples of transforms that operate on a single qubit 102a include the Hadamard gate (a radix-2, 1-qubit Fourier transform), an identity transform (i.e., I, a quantum no-operation), a bit flip (i.e., X, a quantum NOT), a phase flip (i.e., Z, which changes the signs of amplitudes), a bit and phase flip (Y), a rotation by $$\frac{\pi}{4}(S),$$

and a rotation by $$\frac{\pi}{8}(T).$$

In an illustrative embodiment, a quantum gate 1004 performs any number of single qubit operations substantially simultaneously or concurrently.

Figure 11:
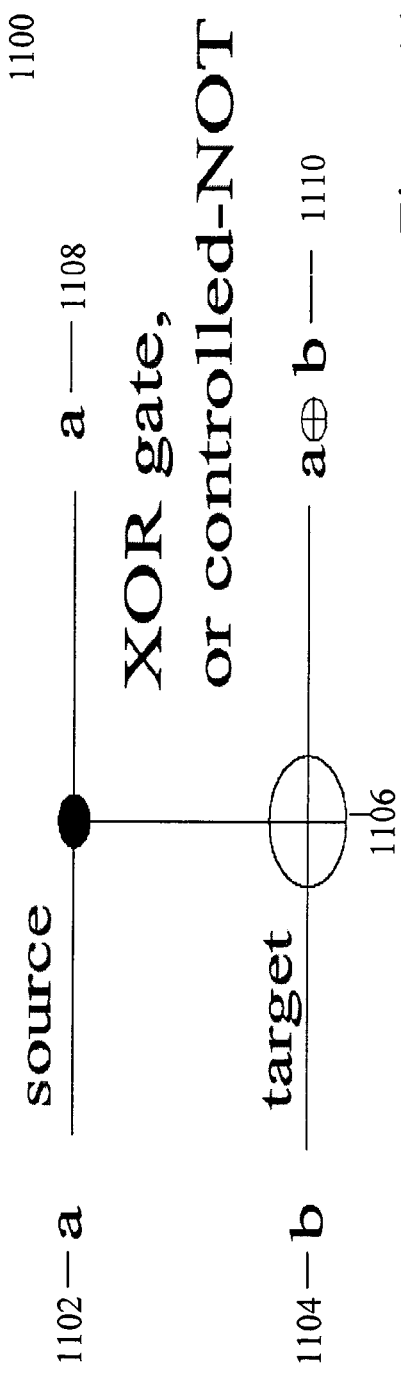
FIG. 11 is a schematic diagram of a two-qubit XOR or controlled-NOT gate of the type employed in an illustrative embodiment of the invention.

FIG. 11 is a schematic diagram of a two-qubit exclusive-OR (XOR) or controlled-NOT (CNOT) gate 1100 used to perform a quantum computation and formed from QIP elements according to the invention. The quantum XOR gate includes two input qubits, one denoted "source" and labeled "a" 1102, and one denoted "target" and labeled "b" 1104.

According to the illustrative embodiment, the qubits are entangled within a single QIP element 100 or alternatively, may be located within different QIP elements 100. FIG. 11 represents the simplest configuration of a reversible quantum logic gate 1004. A controlled-NOT ("CNOT") quantum gate 1100, or quantum XOR gate, is a building block for larger universal quantum gates. The controlled-NOT gate has the following truth table:

| Source Input 1102 | Target Input 1104 | Quantum Input State | Source Output 1108 | XOR Output 1110 | Quantum Output State |
|---|---|---|---|---|---|
| 0 | 0 | \|00> | 0 | 0 | \|00> |
| 0 | 1 | \|01> | 0 | 1 | \|01> |
| 1 | 0 | \|10> | 1 | 1 | \|11> |
| 1 | 1 | \|11> | 1 | 0 | \|10> |

Thus, with the CNOT gate 1100, the output target qubit 1110 is transformed according to the truth table of the exclusive-OR, while the source qubit 1102 is unchanged as the output source qubit. Therefore, the target qubit 1104 undergoes a classical logical NOT operation only if the source qubit 1102 is in the orthogonal state |1>. The retention of the first qubit 1108 makes the quantum XOR gate 1100 reversible—the input is a unique function of the output.

The CNOT gate 1100 supports creation of a universal quantum gate. The universal gate is created by combining the CNOT gate and an arbitrary unitary quantum gate V(θ, φ). The quantum gate V(θ, φ) can be a general rotation of a single qubit 112. V(θ, φ) can be represented by:

$$V(\theta, \phi) = \begin{pmatrix} \cos\left(\frac{\theta}{2}\right) & -ie^{-i\phi}\sin\left(\frac{\theta}{2}\right) \\ -ie^{i\phi}\sin\left(\frac{\theta}{2}\right) & \cos\left(\frac{\theta}{2}\right) \end{pmatrix}$$

where both φ and θ are irrational angles.

Thus, a 2-qubit XOR gate 1100 and a single-qubit rotation gate V(θ, φ) within the QIP element 100 can form any n×n unitary matrix for n qubits. Therefore, the qubits within the QIP element 100 can create a universal quantum gate.

Using the universal quantum gate, the quantum processor 602 can perform quantum calculations. Further, because the QIP element 100 is formed using a bioengineered protein, the cage 106 is highly scalable. For example, in some illustrative embodiments, multiple cages 106 may be physically linked via molecular addends, but are not limited to such addend types. In other illustrative configurations, multiple cages 106 may be functionally linked via photonic, chemical, electromagnetic, electrical and/or quantum (non-classical) interactions, to work and cooperate locally and/or remotely.

Additionally, the cage 106 is insulative. This enables the cage to act as a shielding mechanism and preserve quantum coherence of the overall quantum computer 600. Thus, the storage of the qubits within the clathrin cage 106 enables the decoupling of the qubits from the surrounding environment. In one embodiment, a single qubit comprises a cargo element 102 that renders the clathrin cage 106 itself a single qubit that is entangled with other QIP elements 100. In another embodiment, a plurality of qubits in a single clathrin cage 106 become entangled.

Referring to FIG. 5 above, an XOR gate can be articulated using ENDOR as disclosed by DiVincenzo, incorporated by reference herein. DiVincenzo, D., *Quantum Gates and Circuits,* quant-ph/9705009 (1997). The XOR gate is used to measure the value of the source qubit 1102. As mentioned above, in a preferred embodiment, the qubit is measured nondestructively.

Figure 12:
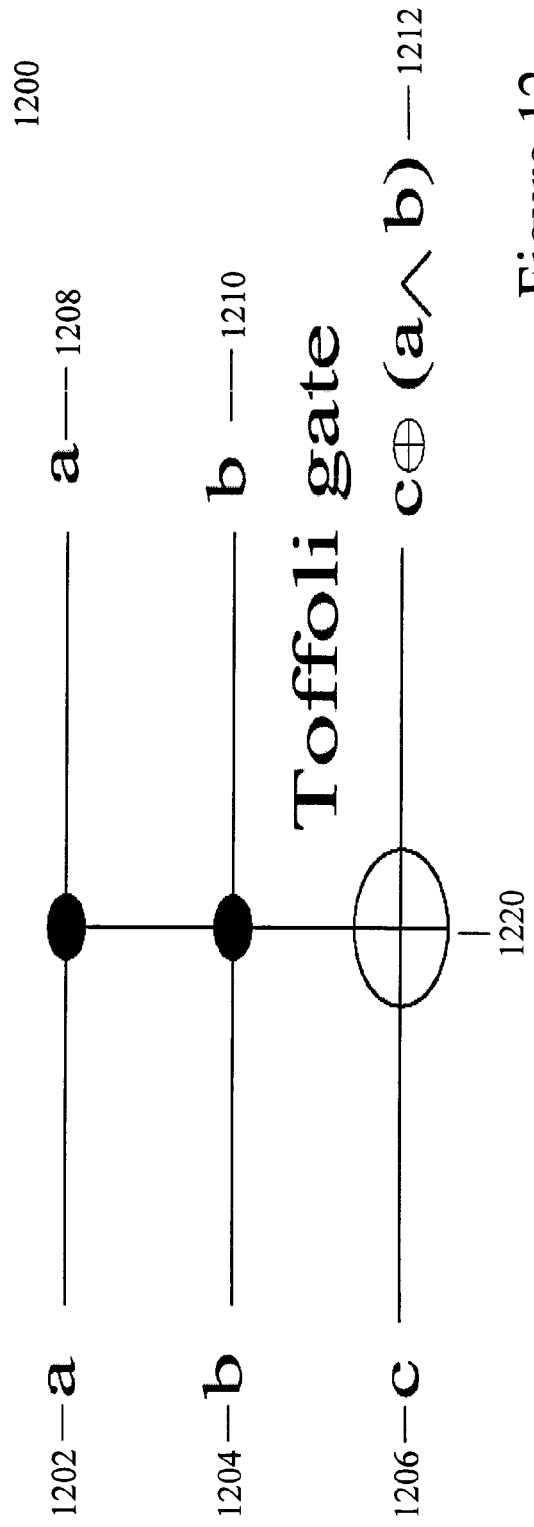
FIG. 12 is a schematic diagram of a three-qubit universal reversible logic gate known as a Toffoli gate of the type employed in an illustrative embodiment of the invention.

FIG. 12 is a schematic diagram of a three-qubit universal reversible logic gate known as a Toffoli gate and formed using QIP elements according to the invention. Universal logic gates are useful because from them a circuit may be assembled to evaluate any Boolean function. In classical logic circuits, the NAND gate is the universal gate, though it is not reversible. A Toffoli gate is the quantum analog of the NAND gate and requires three input qubits 1202, 1204, and 1206. Two of the input qubits remain intact after the XOR operation 1220. The output values 1208 and 1210 of the two unchanged input qubits 1202 and 1204 remain the same. The qubits are saved. The third qubit 1206 is "toggled" by the (a ^ b) operation 1212. The truth table for a Toffoli gate is shown below:

| 1202 | 1204 | 1206 | Quantum input state | 1208 | 1210 | 1212 | Quantum output state |
|---|---|---|---|---|---|---|---|
| 0 | 0 | 0 | \|000> | 0 | 0 | 0 | \|000> |
| 0 | 0 | 1 | \|001> | 0 | 0 | 1 | \|001> |
| 0 | 1 | 0 | \|010> | 0 | 1 | 0 | \|010> |
| 1 | 0 | 0 | \|100> | 1 | 0 | 0 | \|100> |
| 0 | 1 | 1 | \|011> | 0 | 1 | 1 | \|011> |
| 1 | 1 | 0 | \|110> | 1 | 1 | 1 | \|111> |
| 1 | 0 | 1 | \|101> | 1 | 0 | 1 | \|101> |
| 1 | 1 | 1 | \|111> | 1 | 1 | 0 | \|110> |

The universality of a Toffoli gate 1200 can be shown with resort to the analogous digital NAND gate, replacing each NAND with a Toffoli and setting the third qubit 1206 equal to 1.

Figure 13:
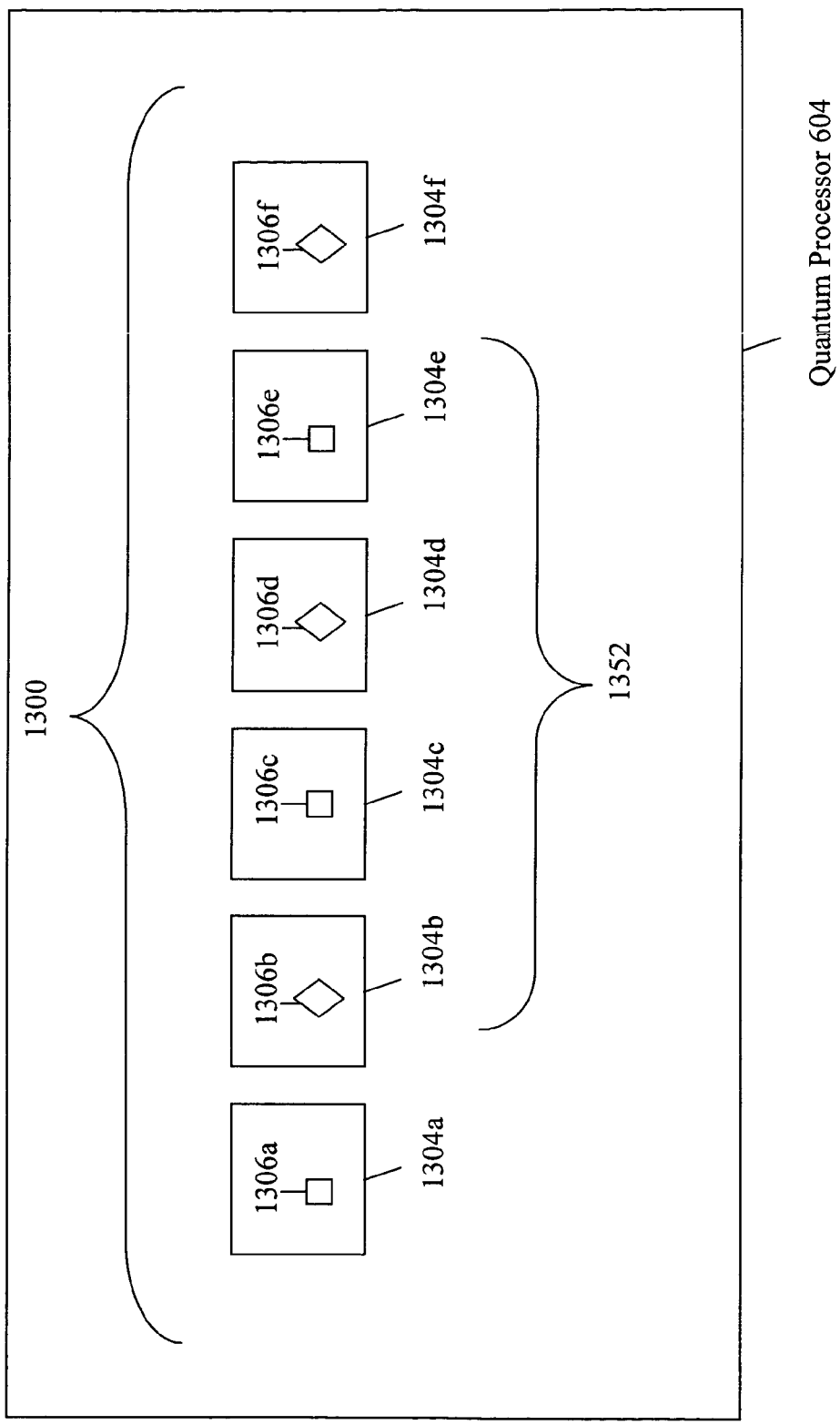
FIG. 13 is a conceptual diagram depicting an illustrative chain of clathrin cages within the quantum processor of FIG. 6.

FIG. 13 is a conceptual diagram depicting a chain of clathrin cages within the quantum processor 602 of FIG. 6. In one illustrative embodiment, the quantum processor 602 includes a chain 1300 of QIP elements 1304a–1304f enclosing cargo elements 1306a–1306f, respectively, of two different quantum states. In particular, the quantum processor 602 utilizes a small number of identifiable spins placed in a regularly spatial pattern. The first 1304a, third 1304c, and fifth 1304e QIP elements each have a respective first 1306a, third 1306c, and fifth 1306e cargo element. The second 1304b, fourth 1304d, and sixth 1304f QIP elements each have a respective second 1306b, fourth 1306d, and sixth 1306f cargo element. The first 1306a, third 1306c, and fifth 1306e cargo elements are also collectively referred to below as an A molecule. Similarly, the second 1306b, fourth 1306d, and sixth 1306f cargo elements are also collectively referred to below as a B molecule. In one illustrative embodiment, utilizing a quantum cellular automata quantum computing architecture, but the invention is not limited to utilizing such architectures, the A and B molecules 1306a–1306f have different, identifiable spin species, and for example, the A and B molecules respectively may correspond to a distinctive chemical variant of a nitroxide molecule. In one illustrative embodiment, either the nuclear spin or the electron spin of the A and B molecules represent qubits. In the illustrative embodiment, the QIP elements 1304a–1304f are arranged in alternating linear patterns such that the molecules form a chain configured alternatively, e.g., ABABAB.

The quantum computer 600 manipulates the quantum information encoded in this spin chain 1300 via global addressing techniques. Thus, in one illustrative embodiment, a qubit is encoded into four spin sites of the cargo elements 1306a–1306f with a buffer space of four empty spin spites between each logical qubit.

To create the quantum gates of FIGS. 11 and 12, a unitary operator $$\hat{A}\frac{U}{f}$$

is first realized. Denoting the spin upstate as |1> and the spin down state as |0>, $$\hat{A}\frac{U}{f}$$

is the conditional application of the unitary U to the A qubits in the alternating qubit chain 1300 ABABAB, depending on the state of A's neighboring B qubits. In a preferred embodiment, the qubits are represented by spin states. Regarding $$\hat{A}\frac{U}{f},$$

ƒ is the sum of the states of the neighboring B spins. Regarding $$\hat{B}\frac{U}{f},$$

ƒ is the sum of the states of the neighboring A spins. Thus, if ƒ=1, $$\hat{A}\frac{U}{1}$$

is the conditioned application of U to all A spins in the alternating chain 1300 which have neighboring B spins that are different from each other. In one embodiment, the I/O module 602 sequences the application of $$\hat{A}\frac{U}{f} \text{ and } \hat{B}\frac{U}{f}$$

to generate the single qubit operations and the two-qubit CNOT operations. In particular, to move quantum information across the cargo elements 1306a–1306f through the spin chain 1300, the quantum I/O module 602 applies an alternating pulse sequence of $$\hat{A}\frac{NOT}{1}$$

followed by $$\hat{B}\frac{NOT}{1},$$

while the generation of a control-U between two neighboring logical qubits requires a predetermined number of global pulses. The application of the above two pulse sequences results in a quantum CNOT gate within the QIP element 1304a. In a preferred embodiment, the global addressing pulses include electromagnetic field pulses that interact with the qubits. In another illustrative embodiment, ENDOR includes the values of the pulses.

Figure 14:
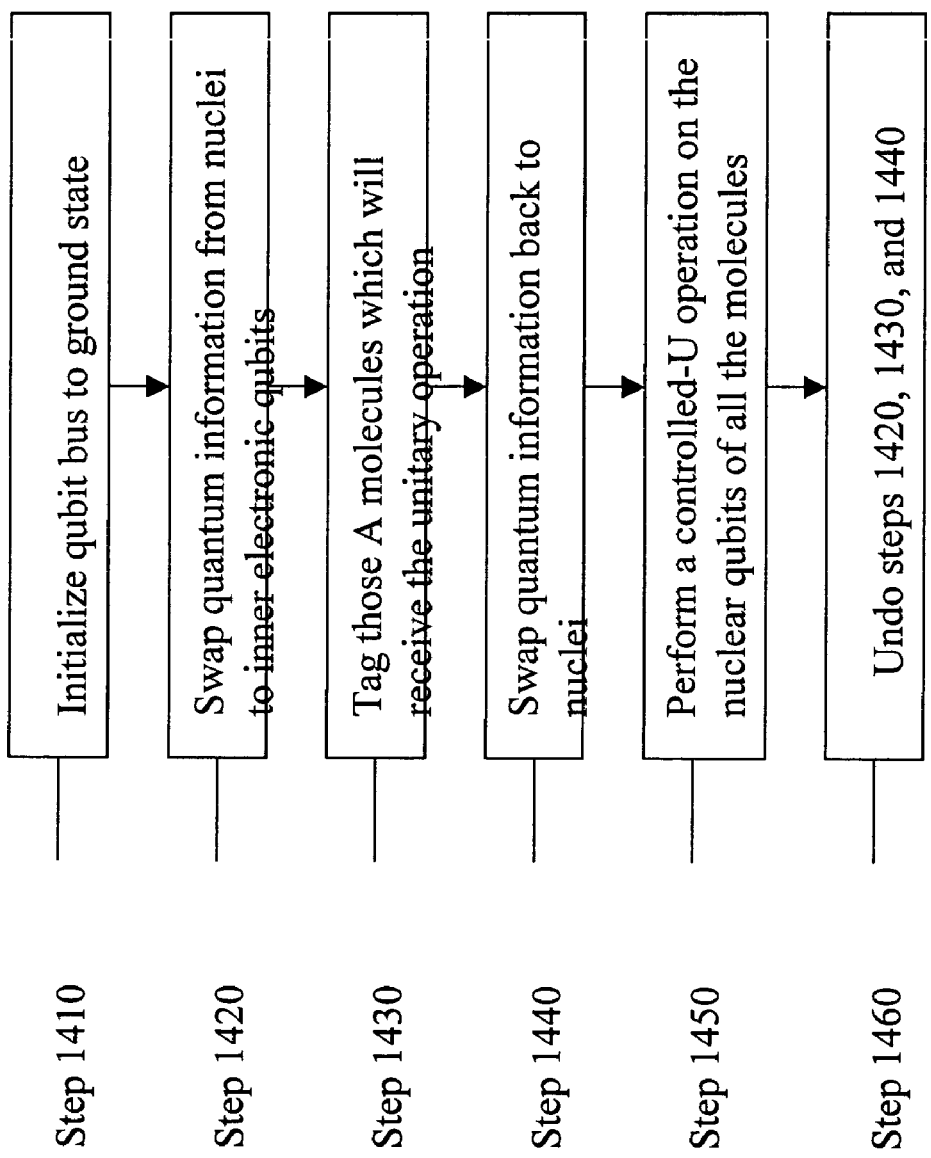
FIG. 14 is a flow diagram depicting exemplary steps performed by the quantum processor of FIG. 6 to perform quantum operations according to an illustrative embodiment of the invention.

FIG. 14 is a flow diagram depicting exemplary steps performed by the quantum processor of FIG. 6 to perform quantum operations. The first step 1410 involves initializing a local qubit bus 1352 to ground state. In a preferred embodiment, the qubits exist within QIP elements 1304a–1304f. In another embodiment, the qubits exist in joined QIP elements 1304a–1304f according to the method of FIG. 10. In one illustrative embodiment, the quantum information is stored in the electron spins of the cargo elements 1306a–1306f. In another illustrative embodiment, the quantum information is stored on the nuclear spin of the cargo elements 1306a–1306f. In one illustrative embodiment, this initialization occurs with a spin cooling quantum algorithm to spin cool all of the nuclear and electron spins to the ground state. In another illustrative embodiment, initialization occurs with spin initialization imposed by an external magnetic field.

Referring again to FIG. 13, to execute a unitary operator, the inner cargo elements 1306b–1306e become a local "bus" 1352 for the quantum information stored in the nuclei of the cargo elements 1306a–1306f that act as qubits. In the illustrative embodiment, the cargo elements 1306a–1306f are molecules whose electron or nuclear spin represent quantum information including qubits. In the illustrative embodiment, the algorithm begins in step 1410 by initializing the bus 1352 to the ground state of a cargo element including nuclear spin as a qubit. Because the nucleus is presumed to be a fermion, it possesses ground state spin denoted by $|m_s\rangle=|-1/2\rangle$ for all of the molecules 1306b–1306e that exist in the bus 1352. According to the illustrative embodiment, this initialization occurs with a spin cooling quantum algorithm to spin cool all of the nuclear and electron spins to the ground state. In a particular embodiment, application of RF waves mediate the spin cooling. Subsequent to the initialization, an arbitrary pattern of quantum information is written onto the nuclear spins of the A and B molecules 1306a–1306f within the clathrin cages 1304a–1304f, respectively. The quantum processor 602 then swaps 1420 the quantum information of the first cargo element 1306a from the nuclei to the electron of the first molecules in the local bus 1306b. In the illustrative embodiment, the swap operation 1420 is performed using multiple CNOT operations using the method described with respect to FIG. 11. The quantum computer 600 then tags 1430 the first cargo element 1306a receiving the unitary operation U in $$\hat{A}\frac{U}{f}$$

by performing a spin-flip on all of the electrons in the bus 1352 in the where the state of neighboring electrons exists in an opposite quantum logic state. The quantum computer 600 then undoes the swapping step 1420 by swapping 1440 the quantum information back into the nucleus of the last cargo element 1304f from the electron of the last cargo element 1306e of the local bus 1352. The quantum state of the information transmission is inferred from the state of the last cargo element 1304f.

The quantum computer 600 then performs a controlled-U operation 1450 on the nuclear qubits of all of the cargo elements 1306a–1306f within the QIP elements 1304a–1304f using the electron qubits of the molecules in the bus 1352 as a control. In one embodiment, the quantum processor performs the controlled-U operation essentially as discussed referring to FIG. 13. In step 1460, the quantum computer 600 undoes the previous steps to initialize the QIP elements 1304a–1304f for the next global operation 1400. Thus, the quantum processor 602 swaps the information from the nucleus to the electron on the first cargo element 1306a, undoes the tagging 1430 of the adjacent molecules 1306b–1306f, respectively, and then swaps 1440 the quantum information back from the electron of the last cargo element onto the nucleus of last cargo element 1306f. The quantum processor 602 consequently re-initializes the system in the manner described above after performing the global operation $$\hat{A}\frac{U}{f}.$$

Figure 15:
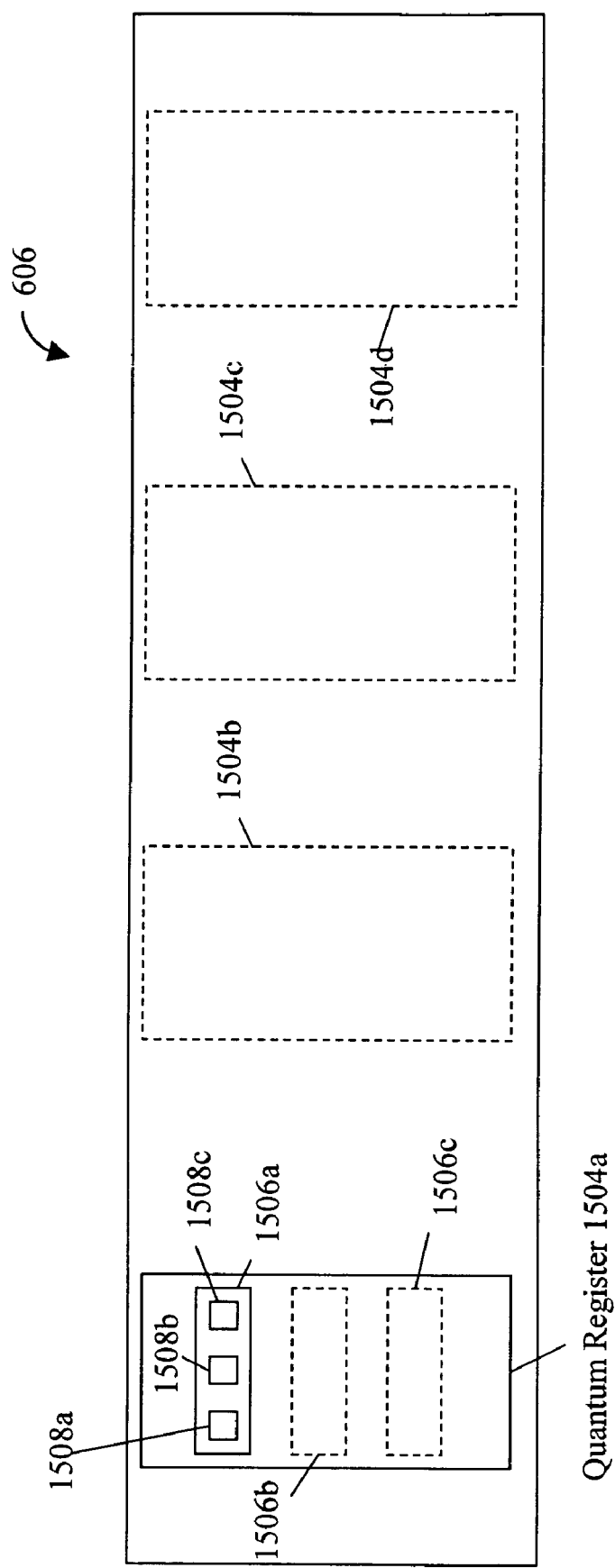
FIG. 15 is a block diagram depicting an illustrative embodiment of the quantum memory of FIG. 6.

FIG. 15 is a block diagram depicting an illustrative embodiment of the quantum memory 606 of FIG. 6. The illustrative quantum memory 606 includes one or more quantum registers 1504a–1504d. The quantum registers 1504a–1504d each include one or more QIP elements 1506a–1506c of the type depicted at 106 in FIG. 1. Each QIP element 1506a–1506c includes one or more cargo elements 1508a–1508c of the type depicted at 102 in FIG. 1. As in FIG. 1, one or more of the cargo elements 1508a–1508c include qubits. The QIP elements 1506a–1506c operate as the respective quantum register 1504a–1504c. As discussed above, due to superposition, each qubit can be programmed into a logic 0, logic 1 or a superposition of both states. For example, the QIP element 1506a carries a first cargo element 1508a including a first qubit, a second cargo element 1508b including a second qubit, and a third cargo element 1508c including a third qubit. Unlike a classical 3-bit register, which can store only one out of eight possible logic states (e.g., 000, 001, 010, etc.) at any one time, a QIP element, such as the QIP element 1506a, can have three qubits storing all eight possible logic states simultaneously at any given moment in time. Further, due to the icosahedral symmetry of the clathrin cage, employed in the illustrative QIP element 1506a it can carry a large number of cargo elements, such as the cargo elements 1508a–1508c, thereby increasing the storage capacity of each QIP element 1506a–1506c.

According to one illustrative embodiment, the total cargo carrying number limit is receptor-type and cargo-type dependent. Cargo size and shape also play a role. The heavy chain terminal domain provides multiple interaction sites for a variety of adaptor proteins that bind ligands. Additionally, molecular tethers and direct cage bonding may be employed in combination with receptors to increase cargo carrying capacity. Also, non-qubit-only QIP elements singly or when chained together, may further increase payload capacity.

In this way, the QIP elements 1506a–1506c perform in an analogous fashion to conventional storage registers, however, with increased storage capacity. As the number of qubits 1508a–1508c increases, the storage capacity of the clathrin cage 1506a increases exponentially (e.g., L qubits can store $2^L$ numbers at once) based on superposition. To increase the storage capacity of the quantum memory 606 even further, any number of QIP elements 1506a–1506c can be linked together according to the method depicted with respect to FIGS. 4 and 10. For example, the QIP element 1506a physically links to a second QIP element 1506b via their respective clathrin cages with molecular addends. Alternatively, for example, the QIP element 1506a functionally links to a second QIP element 1506b via photonic, chemical, electromagnetic, electrical and/or quantum (non-classical) interactions, and so linked can work and cooperate both locally and remotely. Although described above with respect to the QIP elements 1506a–1506c, in one embodiment, the description applies to any number of QIP elements, in any of their embodiments.

Figure 16:
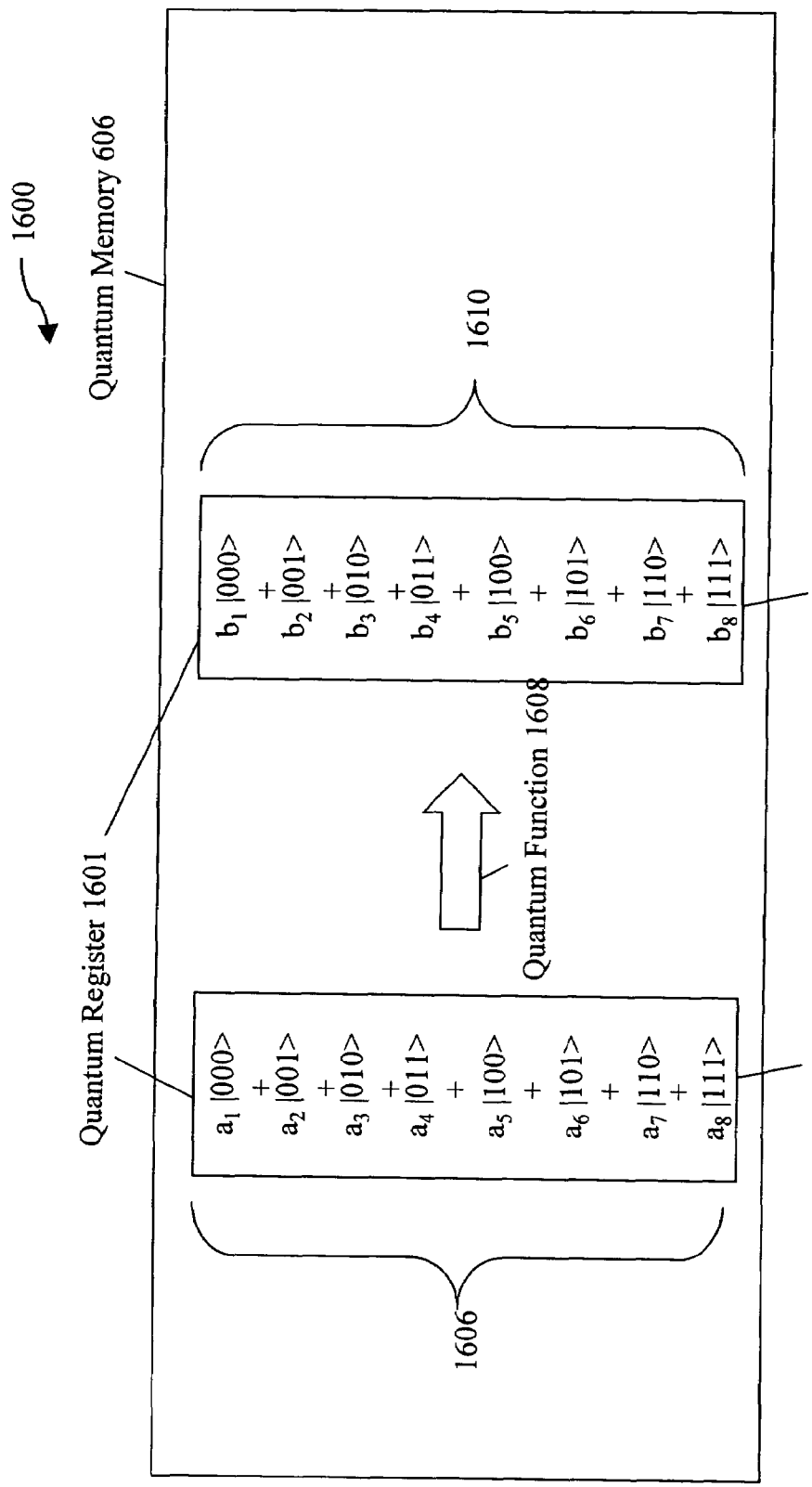
FIG. 16 is a block diagram depicting illustrative states of the quantum memory of FIG. 6.

FIG. 16 is a block diagram depicting illustrative states of the quantum memory 606 of FIG. 6. FIG. 16 shows an illustrative embodiment of a first state 1602 and a second state 1604 of a quantum register 1601 of the type depicted at 1504a in FIG. 15. For simplicity, in the illustrative embodiment of FIG. 16 each QIP element 1506a–1506c is analyzed as having only a single cargo element. However, as discussed above, each QIP element may include any suitable number of cargo elements. As shown, a quantum register 1601, so configured, contains eight possible quantum logic states. When the quantum register 1601 is in a first state 1602, the three qubits (one located in each QIP element 1506a–1506c include all possible three-qubit quantum logic states 1606 simultaneously (because of superposition). Thus, the three qubits include the linear sum of all possible quantum logic states: $a_1|000>+a_2|001>+a_3|010>+a_4|011>+a_5|100>+a_6|101>+a_7|110>+a_8|111>$, where $a_1$–$a_8$ ($a_i$) are unknown coefficients whose normalized probability is unity. When the quantum processor 604 implements a quantum function 1608 on the contents of the quantum register 1601, the processor 604 performs the function 1608 on all of the qubits in the quantum register 1601. Thus, the initial superposed quantum logic states of the qubits evolve into a second superposed quantum logic state 1610. In this second quantum logic state 1610, the quantum logic state may include the same or a different configuration of the qubits and the three qubits include the linear sum of all possible resultant quantum logic states: $b_1|000>+b_2|001>+b_3|010>+b_4|011>+b_5|100>+b_6|101>+b_7|110>+b_8|111>$, where $b_1$–$b_8$ ($b_i$) are unknown coefficients that are the result of the function 1608 on the coefficients of the first quantum logic state 1606. Similar to the $a_i$ coefficients, the normalized probability of the $b_i$ coefficients is unity. Each coefficient $a_i$ and $b_i$ represents a probability amplitude indicating the probability that a measurement will yield the physical logic state associated with that coefficient. In the illustrative embodiment, the quantum processor 604 enables parallel, highly scalable computing by one or more of the QIP elements 1506a–1506c.

The quantum memory 606 utilizes encoded information contained in the decoherence-preventive space of cage 106 or contained in the decoherence-preventive space of vesicle 110 within cage 106. According to one illustrative embodiment, the quantum memory 606 is a single quantum gate in which a light source (e.g., a laser) addresses a single cargo element 102a–102f within a QIP element 100 and to read and write to the QIP element 100. Further, the quantum memory 606 depicted with respect to FIG. 6 uses other QIP techniques known in the art, as the basis of the quantum register 1504a–1504c.

Other illustrative quantum memory 606 room temperature embodiments that utilize techniques known in the art include, but are not limited to: 1) ESR and free radical molecules like nitroxide, wherein the nitroxide molecule acts as long-lived qubit memory; 2) ESR and a quantum dot, wherein the quantum dot is operated as a spin-memory; 3) Laser-based encoding of ions that are confined along the axis of a nanoscale linear radio-frequency (RF) trap; and 4) Using a laser to fully entangle the collective spin of an ensemble of atoms in an atomic vapor that is encapsulated in a cavity.

Some of these 606 memory embodiments, as well as some other QIP element 100 embodiments, may also exploit the Coulomb blockade-like properties of self-assembled proteins, wherein a single particle at a time may move through a transmembrane protein-based channel.

Figure 17:
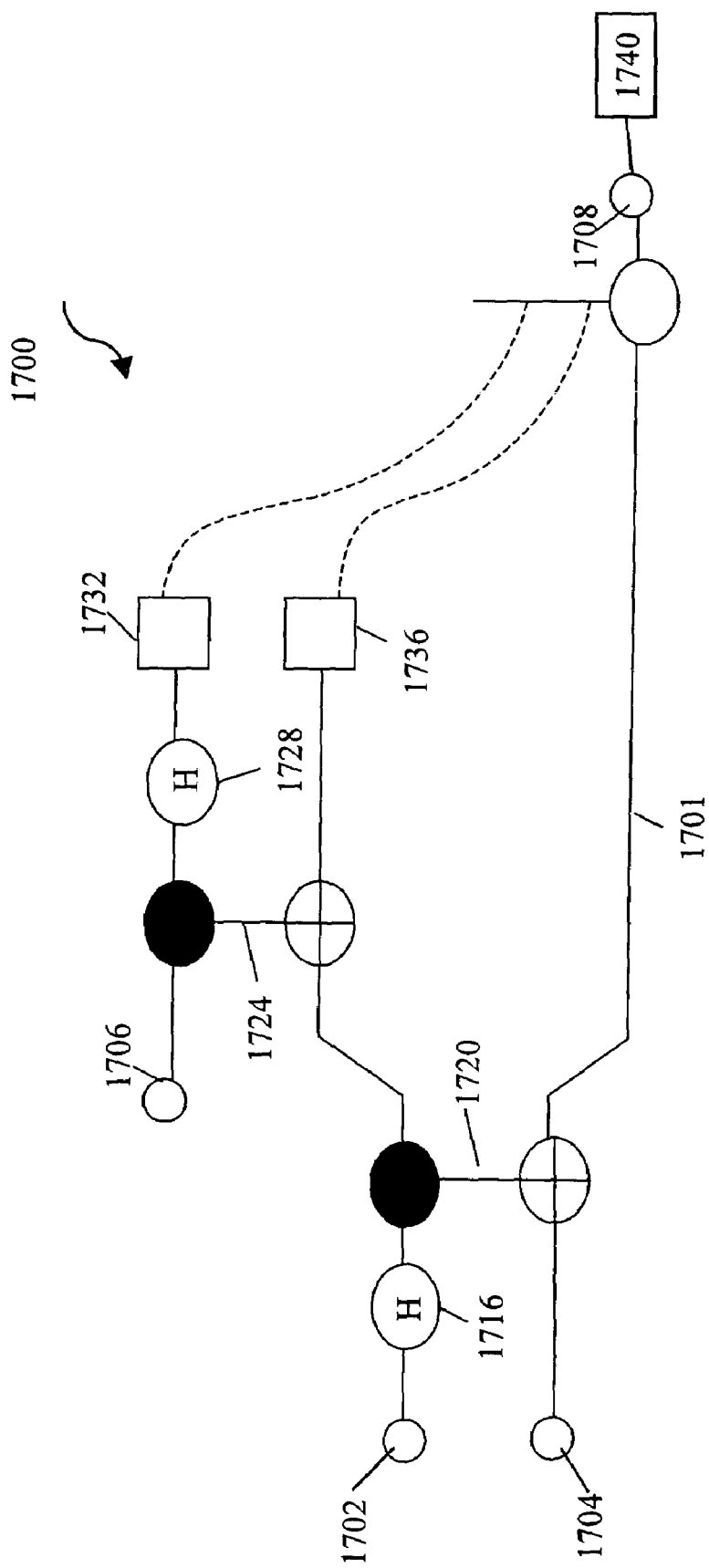
FIG. 17 as a schematic representation of quantum wires enabling clathrin cages to communicate according to an illustrative embodiment of the invention.

FIG. 17 as a conceptual representation 1700 illustrating how QIP elements of the type depicted at 100 in FIG. 1 communicate along a quantum wire 1701 according to an illustrative embodiment of the invention. In a particular illustrative embodiment, the quantum wire 1701 connects the qubits 1704 and 1708 in one or more QIP elements 100.

One illustrative embodiment of the quantum wire 1701 utilizes passing of information along a line of quantum devices, or a "swapping channel", for short communication distances. In some ways, swapping channel quantum wire 1701 resembles a quantum-cellular automata wire, and is similar operation to the ABAB quantum cellular automata architecture embodiment discussed above, except without duplication of data capabilities.

In another illustrative embodiment, the quantum wire 1701 is a coherent quantum nanowire using self-assembled proteins, wherein electron transport is confined to a single dimension and a single electron may be transported over the molecular quantum wire 1701. The molecular quantum wire 1701 may be an angstroms long molecular tether comprised of self-assembled organic compounds, which may also be metal-coated proteins, and which material and structural techniques are known in the art. In one illustrative embodiment, the molecular quantum wire 1701 may be chemically bonded to the qubit cargo elements 102a–102f, which are quantum dots; wherein the spin of a single electron confined in a quantum dot is used as qubit. The quantum wire 1701 may connect and control qubit interactions between the qubits 1704 and 1708, and the quantum wire 1701 may serve multiple functions. The molecular quantum wire 1701 may be an electrically or optically active molecular structure.

Another illustrative embodiment of a quantum wire 1701 is a nano-photonic quantum wire and utilizes an ultrabright, ultralow threshold, Q-switched ARC nanolaser and its strongly directional output. In this embodiment, the nano-photonic quantum wire 1701 is a photonic analog of the molecular electronic quantum wires. In the case of the photonic wire 1701, photons are confined to propagate in one dimension, which leads to a modification of photon density of states. Then nano-photonic quantum wire 1701 may connect the qubits 1704 and 1708 over short, medium and long distances, which distances are dependent on waveguide materials and designs known in the art.

In one illustrative embodiment, the nano-photonic quantum wire 1701 and the quantum memory 606 may be combined with an ultrabright source of polarization-entangled photons generated via an ARC nanolaser, which constitute a QIP platform quantum communications that permit quantum computers to be networked and to enable secure communications.

The QIP elements 100 may also communicate over arbitrarily long distances by transmitting a quantum state between two spatially separated qubits 1704 and 1708, without actually transmitting any quantum data (i.e., teleportation). The location of the first qubit 1706 may be, for example, in a first QIP element, such as the QIP element 100, and the location of the second qubit 1708 may be, for example, in a second, similar QIP element. Steane, incorporated herein by reference, discloses the theory of qubit teleportation. Steane, A., *Quantum Computing,* Rep. Prog. Phys. v. 61, pp. 117–173 (1998).

Time is depicted in FIG. 17 as progressing from left to right. The illustrative example 1700 employs two entangled qubits 1702 and 1704 whose quantum logic state is known and one qubit 1706 whose quantum logic state is unknown. The data carried by the qubit 1706 in the unknown quantum logic state can be nondestructively transmitted to the qubit 1708. In the illustrative embodiment, the entangled pair 1702 and 1704 can be represented by the state |00>+|11>. Without a loss of generality, the state of the qubit 1706 may be depicted by $|\phi>=a|0>+b|1>$ such that a and b are unknown coefficients. $|\phi>$ is the state of the unknown qubit 1706. Thus, the combined quantum logic state of the three qubits 1702, 1704 and 1706 may be represented by:

$a|000>+b|100>+a|011>+b|111>.$

To transmit the unknown state of the qubit 1706 from its location, a Hadamard operation 1716 is applied to the first entangled qubit 1702 and then a CNOT quantum operation 1720 is applied to both qubits 1702 and 1704 in known quantum logic states. Thus, before a quantum computer, such as the quantum computer 600, measures the unknown qubit 1706 and the first entangled qubit 1702, the state is represented by:

$|00>(a|0>+b|1>)+|01>(a|1>+b|0>)+|10>(a|0>-b|1>)+|11>(a|1>-b|0)>$  Equation 1.

The quantum computer 600 then uses a CNOT quantum gate 1724 and a Hadamard gate 1728 to measure the quantum logic state of the unknown qubit 1706. The measurement collapses the combined state of the qubits 1702 and 1704 into one of the four different possibilities represented by each term of Equation 1. In the illustrative embodiment, the measurement yields two classical information bits 1732 and 1736. The quantum computer 600 then transmits the two classical bits 1732 and 1736 to the second location 1708. From the information transmitted by the classical bits 1732 and 1736, it can be determined which of the quantum gates (e.g., I, X, Z, Y), described with respect to FIG. 10, is necessary to place the quantum logic state of the second entangled qubit 1704 into a state such that $a|0>+b|1>=|\phi>$. Thus, the qubit 1708 retrieves the quantum information of the unknown qubit 1706.

The quantum logic state transmitted to the qubit 1708 may later be used as an unknown input quantum state to iterate the cycle. The illustrative transmission of quantum information may be used in quantum error correction described above with respect to FIG. 8. In such an embodiment, the transmitted quantum state may include an input qubit 808, a measurement qubit 818, an ancilla qubit 812, and/or an output qubit 816.

Preferably, a measurement element 1740 of the entangled quantum logic states and the unknown qubit state is realized using ENDOR spectroscopy. In other embodiments, the measurement element is realized using ESR or NMR spectroscopy.

The above described embodiments have been set forth to describe more completely and concretely the present invention, and are not to be construed as limiting the invention. It is further intended that all matter and the description and drawings be interpreted as illustrative and not in a limiting sense. That is, while various embodiments of the invention have been described in detail, other alterations, which will be apparent to those skilled in the art, are intended to be embraced within the spirit and scope of the invention.

What is claimed is:

1. An isolated quantum information processing element comprising
    a cage, up to 100 nanometers in diameter, defining a cavity formed from a plurality of self-assembling purified Clathrin protein molecules, and
    one or more cargo elements located within the cavity, wherein at least one of the cargo elements comprises a qubit programmable into one or more logical states.

2. An isolated quantum information processing element according to claim 1, comprising receptors for capturing and positioning one or more cargo elements within the cavity vesicle.

3. An isolated quantum information processing element according to claim 2, comprising a vesicle located within the cage and enclosing one or more cargo elements, wherein the receptors extend through the vesicle to capture and position a cargo element within the vesicle.

4. An isolated quantum information processing element according to claim 3, comprising adaptors disposed between the receptors and the cage and binding to the receptors.

5. An isolated quantum information processing element according to claim 1, comprising a vesicle located within the cage and enclosing one or more cargo elements.

6. An isolated quantum information processing element according to claim 1, comprising molecular tethers for capturing and positioning one or more cargo elements within and or outside the cavity.

7. An isolated quantum information processing element according to claim 1, comprising direct cage bonding for capturing and positioning one or more cargo elements within the cavity.

8. An isolated quantum information processing element according to claim 1, comprising receptors, molecular tethers and direct cage bonding for capturing and positioning one or more cargo elements within the cavity.

9. An isolated quantum information processing element according to claim 1, wherein the one or more cargo elements of a subset of the quantum information processing elements further comprises a non-permeable cavity.

10. An isolated quantum information processing element according to claim 3, comprising a vesicle forming non-permeable cavity.

11. An isolated quantum information processing element according to claim 1, comprising a self-assembling cage that is electrically neutral and inhibits charge transfer between the cage and its enclosed cargo elements.

12. An isolated quantum information processing element according to claim 1, comprising a self-assembling cage that reduces the tendency of a plurality of logical states in a quantum coherent state to collapse into a classical decoherent state.

13. An isolated quantum information processing element according to claim 1, comprising a non-qubit-only cage that inhibits non-quantum information processing cargo elements from interfering with qubit cargo element operation in one or more other cages.

14. An isolated quantum information processing element according to claim 3, comprising a self-assembling vesicle that is electrically neutral and inhibits charge transfer between the man-made vesicle and its enclosed, cargo elements.

15. An isolated quantum information processing element according to claim 3, comprising an, self-assembling insulative vesicle that reduces the tendency of a plurality of logical states in a quantum coherent state to collapse into a classical decoherent state.

16. An isolated quantum information processing element according to claim 4, comprising self-assembling receptors and adaptors that are electrically neutral and inhibit charge transfer between the vesicle and cage and their enclosed, cargo elements.

17. An isolated quantum information processing element according to claim 1, comprising a self-assembling cage that reduces contaminant background radiation to cargo carried within the cage.

18. An isolated quantum information processing element according to claim 3, comprising self-assembling vesicle that reduces contaminant background radiation to cargo carried within the vesicle.

19. An isolated quantum information processing element according to claim 1, comprising self-assembling framework of cages that structurally support one or more self-assembling quantum information processing elements.

20. An isolated quantum information processing element according to claim 1, comprising a self-assembling, electrically neutral substrate of cages to structurally support one or more of the self-assembling, quantum information processing elements.

21. An isolated quantum information processing element according to claim 1, comprising a self-assembling framework of cages to structurally order one or more self-aligning quantum information processing elements.

22. An isolated quantum information processing element according to claim 1, wherein a cage is empty and includes no cargo elements.

23. An isolated quantum information processing element according to claim 1, wherein the one or more cargo elements is a single cargo element comprising a qubit programmable into one or more logical states.

24. An isolated quantum information processing element according to claim 1, wherein the one or more cargo elements are a plurality of cargo elements.

25. An isolated quantum information processing element according to claim 24, wherein the plurality of cargo elements are qubits programmable into a plurality of logical states.

26. An isolated quantum information processing element according to claim 24, wherein at least some of the plurality of cargo elements are quantum information processing cargo elements.

27. An isolated quantum information processing element according to claim 24, wherein at least some of the plurality of cargo elements are non-quantum information processing cargo elements.

28. An isolated quantum information processing element according to claim 1, wherein the cargo elements respond to stimuli internal and external to the cage.

29. An isolated quantum information processing element according to claim 3, wherein a man-made vesicle and its contained cargo elements respond to stimuli internal and external to the vesicle.

30. An isolated quantum information processing element according to claim 24, wherein a subset of the non-quantum information processing cargo elements include one or more therapeutic.

31. An isolated quantum information processing element according to claim 24, wherein a subset of qubit cargo elements include one or more quantum dots.

32. An isolated quantum information processing element according to claim 24, wherein a subset of the cargo elements include one or more, photonic dots.

33. An isolated quantum information processing element according to claim 24, wherein a subset of the cargo elements include one or more liquids without dopants or with one or more dopants of any suitable type.

34. An isolated quantum information processing element according to claim 24, wherein a subset of the artificially configured cargo elements include a gas or vapor without dopants or with one or more dopants of any suitable type.

35. An isolated quantum information processing element according to claim 1, wherein one or more qubit cargo elements are programmed by one or more pulses of electromagnetic radiation.

36. An isolated quantum information processing element according to claim 1, wherein the qubit includes an unpaired electron and the plurality of logical states of the qubit are defined by spin polarization.

37. An isolated quantum information processing element according to claim 1, wherein the qubit includes a nitroxide molecule.

38. An isolated quantum information processing element according to claim 1, wherein the qubit is photon-based and the plurality of logical states of the photon-based qubit include coherent logical state.

39. An isolated quantum information processing element according to claim 1, wherein the plurality of logical states includes coherent state.

40. An isolated quantum information processing element according to claim 1, wherein the plurality of logical states includes a coherent state at room temperature.

41. An isolated quantum information processing element according to claim 1, wherein the self-assembling protein molecule is a purified clathrin molecule.

42. An isolated quantum information processing element according to claim 1, wherein the cage comprises self-assembling synthetic protein molecules.

43. An isolated quantum information processing element according to claim 4, wherein receptors, adaptors, and vesicle comprise natural and or synthetic protein molecules.

44. An isolated quantum information processing element according to claim 1, comprising a coating on part or the entirety of the cage.

45. An isolated quantum information processing element according to claim 4, comprising a coating on a portion or an entirety of the receptors, adaptors, and vesicles.

46. An isolated quantum information processing element according to claim 1, wherein the cage is substantially greater than one nanometer in diameter.

47. An isolated quantum information processing element according to claim 1, wherein the cage is at least about 50 nanometers in diameter.

48. An isolated quantum information processing element according to claim 1, wherein the cage is at least about 100 nanometers in diameter.

49. An isolated quantum information processing element according to claim 1, wherein the cage is symmetric with respect to a plane.

50. An isolated quantum information processing element according to claim 1, wherein the cage has icosahedral geometry.

51. An isolated quantum information processing element according to claim 1, wherein qubits are linearly positioned at vertices along a single plane using circulant ordering.

52. An isolated quantum information processing element according to claim 1, wherein multiple quantum information processing elements are physically linked together.

53. An isolated quantum information processing element according to claim 1, wherein multiple, self-assembling quantum information processing elements are functionally linked together.

54. An isolated quantum information processing element according to claim 1, wherein the quantum information processing element forms a hybrid system.

55. A method for forming quantum information processing element comprising
- a cage, up to 100 nanometers in diameter, defining a cavity from a plurality of self-assembling purified Clathrin protein molecules, and
- one or more cargo elements located within the cavity, wherein at least one of the cargo elements comprises a qubit programmable into one or more logical states.

56. An isolated quantum information processing element according to claim 1, wherein the quantum information processing element comprises,
- a functionalized, cage for attaching one or more elements external to the cage.

* * * * *